US009020225B2

(12) United States Patent
Sato et al.

(10) Patent No.: US 9,020,225 B2
(45) Date of Patent: Apr. 28, 2015

(54) MEDICAL IMAGE PROCESSING SYSTEM

(71) Applicants: Kabushiki Kaisha Toshiba, Tokyo (JP); Toshiba Medical Systems Corporation, Otawara-shi (JP)

(72) Inventors: Katsunori Sato, Utsunomiya (JP); Kohki Fujii, Utsunomiya (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 70 days.

(21) Appl. No.: 13/785,004

(22) Filed: Mar. 5, 2013

(65) Prior Publication Data
US 2013/0243282 A1    Sep. 19, 2013

(30) Foreign Application Priority Data

Mar. 5, 2012   (JP) ................................. 2012-047913

(51) Int. Cl.
*G06F 19/00*    (2011.01)
*G06F 9/50*    (2006.01)

(52) U.S. Cl.
CPC .............. *G06F 19/321* (2013.01); *G06F 9/505* (2013.01)

(58) Field of Classification Search
CPC ..... G06F 19/321; G06F 19/32; G06F 19/327; G06F 9/505
USPC .................................. 382/128, 304; 718/105
See application file for complete search history.

(56) References Cited

U.S. PATENT DOCUMENTS

| 4,495,562 | A  | * | 1/1985 | Yamaji et al. | .................. | 718/105 |
| 7,483,557 | B2 | * | 1/2009 | Masuzawa et al. | ............ | 382/131 |
| 7,600,229 | B1 | * | 10/2009 | Shmuylovich et al. | ........ | 718/105 |
| 8,032,888 | B2 | * | 10/2011 | Vengerov et al. | ............. | 718/102 |
| 8,341,216 | B2 | * | 12/2012 | Cok | ............................... | 709/203 |
| 8,413,155 | B2 | * | 4/2013 | Jackson | ........................ | 718/104 |
| 8,458,719 | B2 | * | 6/2013 | Wellerdiek | .................... | 718/105 |
| 2009/0064154 | A1 | * | 3/2009 | Aulbach | ........................ | 718/103 |
| 2009/0182879 | A1 | * | 7/2009 | Becker et al. | .................. | 709/226 |
| 2011/0004882 | A1 | * | 1/2011 | Vengerov et al. | ............. | 718/103 |

(Continued)

FOREIGN PATENT DOCUMENTS

| JP | 2002042001 | A | * | 2/2002 | ............. | G06F 17/60 |
| JP | 2009-258777 | | | 11/2009 | | |
| JP | 2013214295 | A | * | 10/2013 | ............. | G60Q 50/24 |

*Primary Examiner* — Kim Vu
*Assistant Examiner* — Molly Delaney
(74) *Attorney, Agent, or Firm* — Oblon, McClelland, Maier & Neustadt, L.L.P.

(57) ABSTRACT

A medical image processing system in which the generation of a non-steady load is made predictable based on the reservation of image processes, includes a reservation manager to manage the process commencement time and the process termination time of the reserved image processing and the amount of medical image data, which is the subject of image processing, a throughput calculating unit to calculate the throughput processed for each predetermined time width in the image processing regarding each image process carried out in the first server, and an analyzing unit to calculate the total throughput of the image processing carried out in parallel for each time width. When the calculated total is more than the predetermined throughput, the analyzing unit specifies at least one from among all image processes carried out in the time width such that the total throughput of a first server becomes less than the predetermined throughput.

9 Claims, 21 Drawing Sheets

(56) References Cited

U.S. PATENT DOCUMENTS

| | | | |
|---|---|---|---|
| 2011/0142357 A1* | 6/2011 | Chang et al. | 382/234 |
| 2011/0154355 A1* | 6/2011 | Becker et al. | 718/104 |
| 2011/0185364 A1* | 7/2011 | Fernandes et al. | 718/104 |
| 2011/0235513 A1* | 9/2011 | Ali | 370/232 |
| 2011/0292466 A1* | 12/2011 | Kino | 358/474 |
| 2012/0069372 A1* | 3/2012 | Hasegawa | 358/1.13 |
| 2013/0204976 A1* | 8/2013 | Okuyama et al. | 709/219 |
| 2013/0243282 A1* | 9/2013 | Sato et al. | 382/128 |

* cited by examiner

FIG. 4

TBL10

| C11 TEST IDENTIFIER | C12 IMAGING PART IDENTIFIER | C13 TEST COMMENCEMENT TIME | C14 TEST TERMINATION TIME | C15 IMAGE PROCESSING CATEGORY | C16 IMAGE SIZE | C17 NUMBER OF IMAGES | C18 RETURN DESTINATION | C19 FILE NAME |
|---|---|---|---|---|---|---|---|---|
| TEST a | IMAGING PART 15A | Ta1 | Ta2 | CATEGORY M11 | CONDITION P11 | Na | TERMINAL 3A | — |
| TEST b | IMAGING PART 15A | Tb1 | Tb2 | CATEGORY M22 | CONDITION P21 | Nb | TERMINAL 3B | — |
| TEST c | — | Tc3 | Tc4 | CATEGORY M12 | CONDITION P12 | Nc | TERMINAL 3C | FILE Fc |
| TEST d | IMAGING PART 15B | Td1 | Td2 | CATEGORY M31 | CONDITION P31 | Nd | TERMINAL 3B | — |
| ...... | ...... | ...... | ...... | ...... | ...... | ...... | ...... | ...... |

FIG. 5

TBL20

| IMAGE PROCESSING CATEGORY (C15) | IMAGE CLASSIFICATION (MODALITY) (C21) | PROCESSING CONTENT (C22) | | |
|---|---|---|---|---|
| CATEGORY M11 | MOD1 | PROCESSING 1 | PROCESSING 2 | PROCESSING 3 |
| CATEGORY M12 | MOD1 | PROCESSING 1 | PROCESSING 2 | PROCESSING 5 |
| ⋮ | ⋮ | ⋮ | ⋮ | ⋮ |
| CATEGORY M21 | MOD2 | PROCESSING 1 | PROCESSING 4 | PROCESSING 3 |
| CATEGORY M22 | MOD2 | PROCESSING 1 | PROCESSING 4 | PROCESSING 5 |
| ⋮ | ⋮ | ⋮ | ⋮ | ⋮ |
| CATEGORY M31 | MOD3 | PROCESSING 6 | PROCESSING 7 | PROCESSING 8 |

FIG. 6

| IMAGE CLASSIFICATION (MODALITY) | IMAGE SIZE | PROCESSING | DATA VOLUME |
|---|---|---|---|
| MOD1 | CONDITION P11 | PROCESSING 1 | D111 |
| MOD1 | CONDITION P11 | PROCESSING 2 | D112 |
| MOD1 | CONDITION P11 | PROCESSING 3 | D113 |
| MOD1 | CONDITION P12 | PROCESSING 1 | D121 |
| MOD1 | CONDITION P12 | PROCESSING 2 | D122 |
| MOD1 | CONDITION P12 | PROCESSING 3 | D123 |
| ⋮ | ⋮ | ⋮ | ⋮ |
| MOD2 | CONDITION P21 | PROCESSING 1 | D211 |
| MOD2 | CONDITION P21 | PROCESSING 3 | D213 |
| MOD2 | CONDITION P21 | PROCESSING 4 | t214 |
| ⋮ | ⋮ | ⋮ | ⋮ |
| MOD3 | CONDITION P31 | PROCESSING 6 | D316 |
| MOD3 | CONDITION P31 | PROCESSING 7 | D317 |
| MOD3 | CONDITION P31 | PROCESSING 8 | D318 |
| ⋮ | ⋮ | ⋮ | ⋮ |

FIG. 7

TBL40

| TEST IDENTIFIER (C11) | TEST COMMENCEMENT TIME (C13) | TEST TERMINATION TIME (C14) | PROCESS COMMENCEMENT TIME (C41) | PROCESS TERMINATION TIME (C42) | THROUGHPUT FOR EACH UNIT TIME (C43) |
|---|---|---|---|---|---|
| TEST a | Ta1 | Ta2 | Ta3 | Ta4 | Da |
| TEST b | Tb1 | Tb2 | Tb3 | Tb4 | Db |
| TEST c | Tc3 | Tc4 | Tc3 | Tc4 | Dc |
| TEST d | Td1 | Td2 | Td3 | Td4 | Dd |

FIG. 14

TBL50

| SERVER IDENTIFIER (C51) | EXECUTABLE IMAGE PROCESSING CLASSIFICATION (C52) | | | |
|---|---|---|---|---|
| SERVER 2C | PROCESS 1 | PROCESS 2 | PROCESS 5 | PROCESS 6 |
| SERVER 2D | PROCESS 3 | PROCESS 4 | PROCESS 7 | PROCESS 8 |
| ⋮ | ⋮ | ⋮ | ⋮ | ⋮ |

FIG. 16

TBL10

| TEST IDENTIFIER (C11) | IMAGING PART IDENTIFIER (C12) | TEST COMMENCEMENT TIME (C13) | TEST TERMINATION TIME (C14) | IMAGE PROCESSING CATEGORY (C15) | IMAGE SIZE (C16) | NUMBER OF IMAGES (C17) | RETURN DESTINATION (C18) | FILE NAME (C19) |
|---|---|---|---|---|---|---|---|---|
| TEST a | IMAGING PART 15A | Ta1 | Ta2 | CATEGORY M11 | CONDITION P11 | Na | TERMINAL 3A | — |
| TEST b | IMAGING PART 15A | Tb1 | Tb2 | CATEGORY M22 | CONDITION P21 | Nb | TERMINAL 3B | — |
| TEST c | — | Tc3 | Tc4 | CATEGORY M12 | CONDITION P12 | Nc | TERMINAL 3C | FILE Fc |
| TEST e | IMAGING PART 15A | Te1 | Te2 | — | — | — | TERMINAL 3A | — |

FIG. 17

TBL40

| TEST IDENTIFIER (C11) | TEST COMMENCEMENT TIME (C13) | TEST TERMINATION TIME (C14) | PROCESS COMMENCEMENT TIME (C41) | PROCESS TERMINATION TIME (C42) | THROUGHPUT FOR EACH UNIT TIME (C43) |
|---|---|---|---|---|---|
| TEST a | Ta1 | Ta2 | Ta3 | Ta4 | Da |
| TEST b | Tb1 | Tb2 | Tb3 | Tb4 | Db |
| TEST c | Tc3 | Tc4 | Tc3 | Tc4 | Dc |

| TEST e | Te1 | Te2 | Te3 | Te4 | De |

MEDICAL IMAGE PROCESSING SYSTEM

CROSS-REFERENCE TO RELATED APPLICATION

This application is based upon and claims the benefit of priority from Japanese Patent Applications No. 2012-047913 filed on Mar. 5, 2012; the entire contents of which are incorporated herein by reference.

FIELD

The embodiment relates to the technology of a medical image processing system that processes medical image data obtained using a medical image imaging device.

BACKGROUND

Medical image data obtained by scanning a patient using a medical image imaging device (also referred to as a modality) may be displayed on a display as an image after undergoing image processing. The medical image imaging device herein includes, for example, an ultrasound diagnostic apparatus, an X-ray diagnostic apparatus, an MRI apparatus (Magnetic Resonance Imaging), an X-ray CT apparatus, etc. These medical image imaging devices and medical image processing systems include a server comprising an image processor that processes images with respect to the image data.

The server carrying out image processing on the image data executes multiple image processes in parallel within its permissible processing capacity range (for example, the throughput of CPU, memory, etc.), thereby shortening the processing time of multiple image processing.

However, the throughput of image processing that may be carried out using a single server is restricted by the processing capacity of the server. Accordingly, when the throughput of the image processing required for the entire system exceeds the throughput of one server, there are cases in which a method is used of sharing image processing between a plurality of servers. In this way, the processing load of each server may be reduced, and the maximum simultaneous feasible throughput may be increased.

When sharing image processing between a plurality of servers, the maximum throughput is predicted based on the predicted number of reserved scans using a scanning apparatus (the number of reserved scans) and the predicted amount of image data to be acquired, after which the number of servers to be installed is determined in correspondence with this maximum throughput.

However, the number of reserved scans and the amount of image data to be scanned is not always constant. For example, the throughput required for the system temporarily increases at periods and times when reservations for scanning concentrate. Moreover, the amount of image data differs depending on the test conditions; for example, when there is a concentration of tests accompanying scanning large images and scanning with numerous scans, the throughput required for the system temporarily increases. In the conventional method, the maximum throughput was predicted including load in such non-ready states (hereinafter, referred to as "non-ready state load"), and more servers were installed as needed.

However, when the incidence of a non-ready state load is low, the resource of the servers increased upon this prediction cannot be effectively used, and the cost benefit from increasing servers is low. Moreover, the non-ready state load is caused by uncertain elements such as the number of reserved scans, scanning conditions, etc., making it difficult to predict correct values in advance.

BRIEF DESCRIPTION OF THE DRAWINGS

FIG. 4 is an example of the reservation management table managing the reservations for examination.
FIG. 5 is an example of the management table that manages the correspondence of the image processing categories with the imaging carried out.
FIG. 6 is an example of the management table that manages the process time for each image process.
FIG. 7 is an example of the process management table that manages the process commencement time and the termination time of image processing.
FIG. 14 is an example of a function management table.
FIG. 16 is an example of the reservation management table pertaining to Embodiment 2.
FIG. 17 is an example of the process management table pertaining to Embodiment 2.

DETAILED DESCRIPTION

The purpose of the present embodiment is to provide a medical image processing system capable of predicting the development of a non-steady load. In order to achieve the purpose, the embodiment is a medical image processing system comprising an image processor that carries out a plurality of image processes in parallel with respect to the medical image data. The medical image processing system comprises a reservation manager, a throughput calculating unit, an analyzing unit, and a request unit. The reservation manager receives reservations for image processing, and manages the process commencement time and process termination time of the reserved image process and the amount of image data, which is the processing subject of the image processing for each image process based on the reservation. The throughput calculating unit calculates the throughput processed for each predetermined time width in the image processing based on the process commencement time and process termination time and the data volume regarding each image process carried out in the first server from among the plurality of servers. The analyzing unit calculates the throughput of image processing carried out in parallel in the time width for the respective time widths based on the commencement time and process termination time of the image processing and the throughput of the image processing carried out in the first server. Moreover, when the calculated total is more than the predetermined throughput, the analyzing unit specifies the first image process comprising at least one from among all image processes carried out in the time width such that the total throughput of the first server becomes less than the predetermined throughput. The request unit requests the first image process to the second server, which differs from the first server.

(Embodiment 1)

Figure 1:
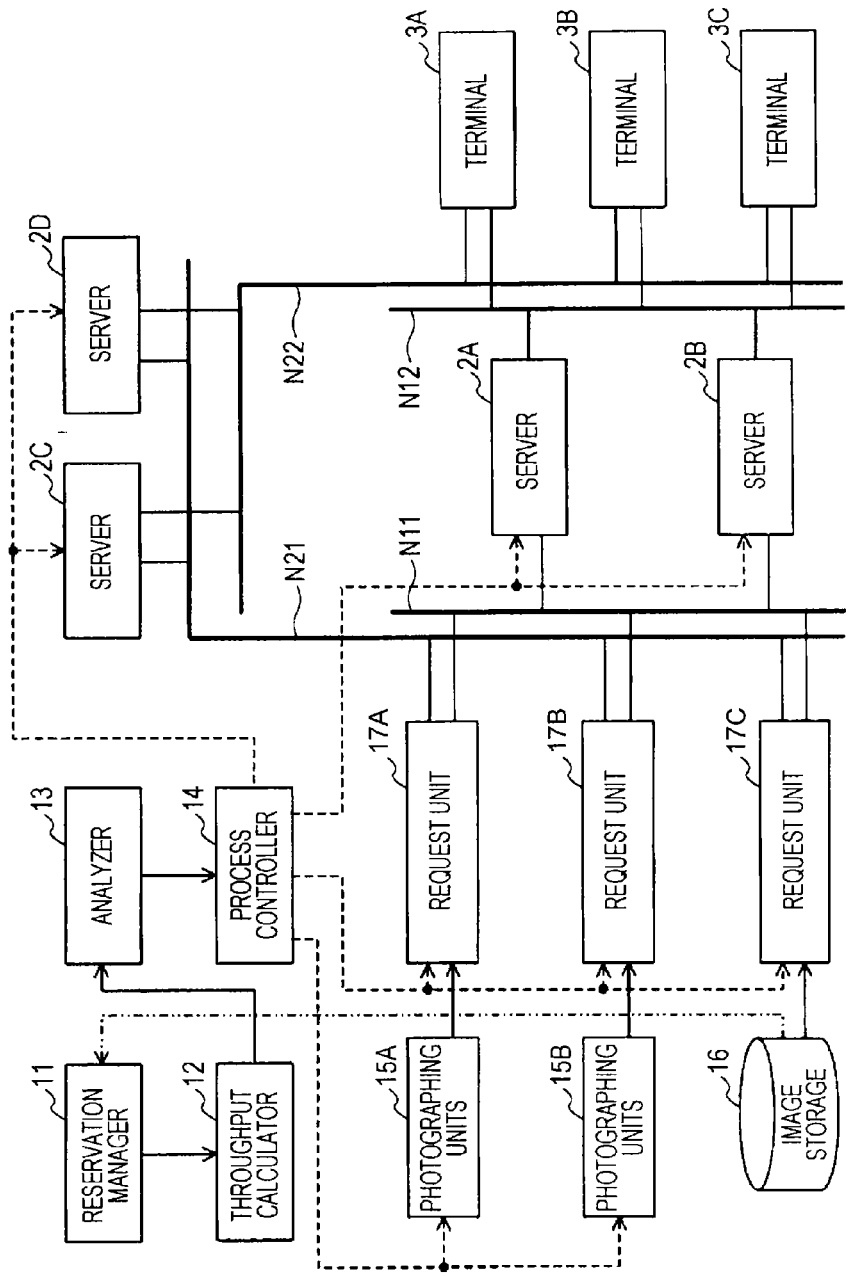
FIG. 1 is a block diagram of the medical image processing system related to the present embodiment.

The medical image processing system pertaining to Embodiment 1 is described with reference to FIG. 1 to FIG. 3. As shown in FIG. 1, the medical image processing system pertaining to the present embodiment comprises a reservation manager 11, a throughput calculator 12, an analyzer 13, a process controller 14, a plurality of modalities (photographing units 15A and 15B, or modalities 15A and 15B), an image storage 16, requests units 17A, 17B, and 17C, hereinafter collectively referred to as "request unit 17", a plurality of servers (that is, servers 2A to 2D), and a plurality of clients (terminals/workstations 3A to 3C).

Servers 2A to 2D are servers for executing image processing with respect to the image data. The detailed configuration of servers 2A to 2D is described later. Moreover, terminals (clients/workstations) 3A to 3C are terminals (clients/workstations) for receiving results from image processing in servers 2A to 2D and displaying the image data on the display (not illustrated). Furthermore, when servers 2A to 2D are not particularly distinguished, these may be simply referred to as "server 2." In the same manner, when terminals (clients/workstations) 3A to 3C are not particularly distinguished, these may be simply referred to as "terminal (clients/workstations) 3."

Servers 2A and 2B are connected via the request unit 17 and a network N11. Moreover, servers 2A and 2B are connected via terminals (clients/workstations) 3A to 3C and network N12. In the same manner, servers 2C and 2D are connected via the request unit 17 and a network N21. Moreover, servers 2C and 2D are connected via terminals (clients/workstations) 3A to 3C and network N22. In this manner, the servers 2A and 2B as well as servers 2C and 2D are connected to the request unit 17 and terminals (clients/workstations) 3A to 3C via differing networks N11 and N12 as well as N21 and N22. As a detailed example, networks N11 and N12 indicate an in-hospital network inside a hospital, while networks N21 and N22 indicate the network to institutes outside the hospital. Furthermore, the abovementioned is only one example, and networks N11 and N12 may be constructed as one network. In the same manner, networks N21 and N22 may be constructed as one network. Moreover, networks N11 and N12 as well as networks N21 and N22 may be constructed as one network without differentiating them. Hereinafter, descriptions are provided assuming that networks N11, N12, N21, and N22 are each independently provided.

In the medical image processing system pertaining to the present embodiment, servers 2A and 2B connected to networks N11 and N12 are determined as the main server (hereinafter, they may be referred to as the "main server"), and servers 2C and 2D connected to networks N21 and N22 are actuated as having a supporting role (hereinafter, they may be referred to as a "supporting server"). Specifically, image processing is mainly carried out by the main server while the supporting server substitutes some image processing when the processing load becomes high, exceeding the processing capacity of the main server. Hereinafter, the predicted processing load of the main server (servers 2A or 2B) will be described along with the mechanism of having the supporting server (servers 2C or 2D) substitute the part of image processing when the predicted processing load exceeds the processing capacity of the main server.

Modalities 15A and 15B are imaging devices for medical image that capture the image data. The photographing reservation for capturing the image data using modalities 15A and 15B is received and managed in the reservation manager 11. Moreover, operation of modalities 15A and 15B is controlled by the process controller 14 based on the photographing reservation received by the reservation manager 11. The reservation manager 11 and the process controller 14 are mentioned later. Furthermore, hereinafter, when modalities 15A and 15B are not particularly distinguished, they may be simply referred to as an "modality 15." In the modality 15, the photographed image data is output to the request unit 17. The request unit 17 is mentioned later.

The image storage 16 is storage that stores image data. Image data that has been photographed in advance is stored in the image storage 16.

(Reservation Manager 11)

Figure 2:
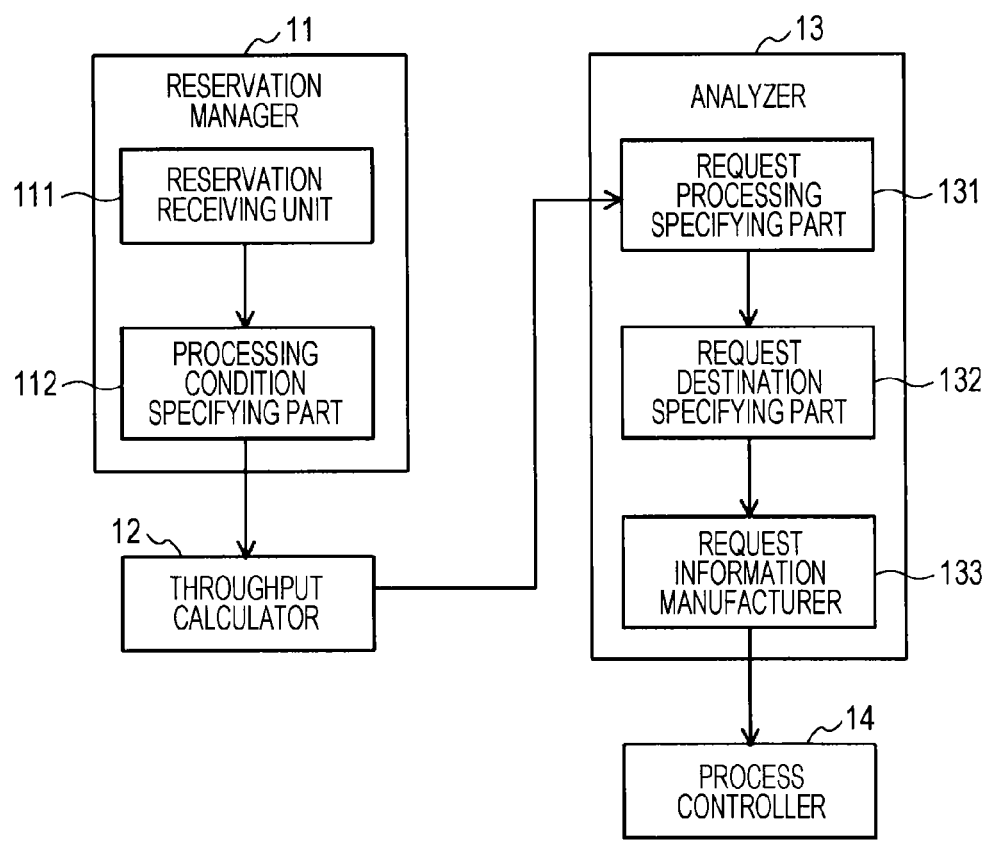
FIG. 2 is a block diagram showing detailed configurations of the reservation manager and the analyzing unit.
Figure 3:
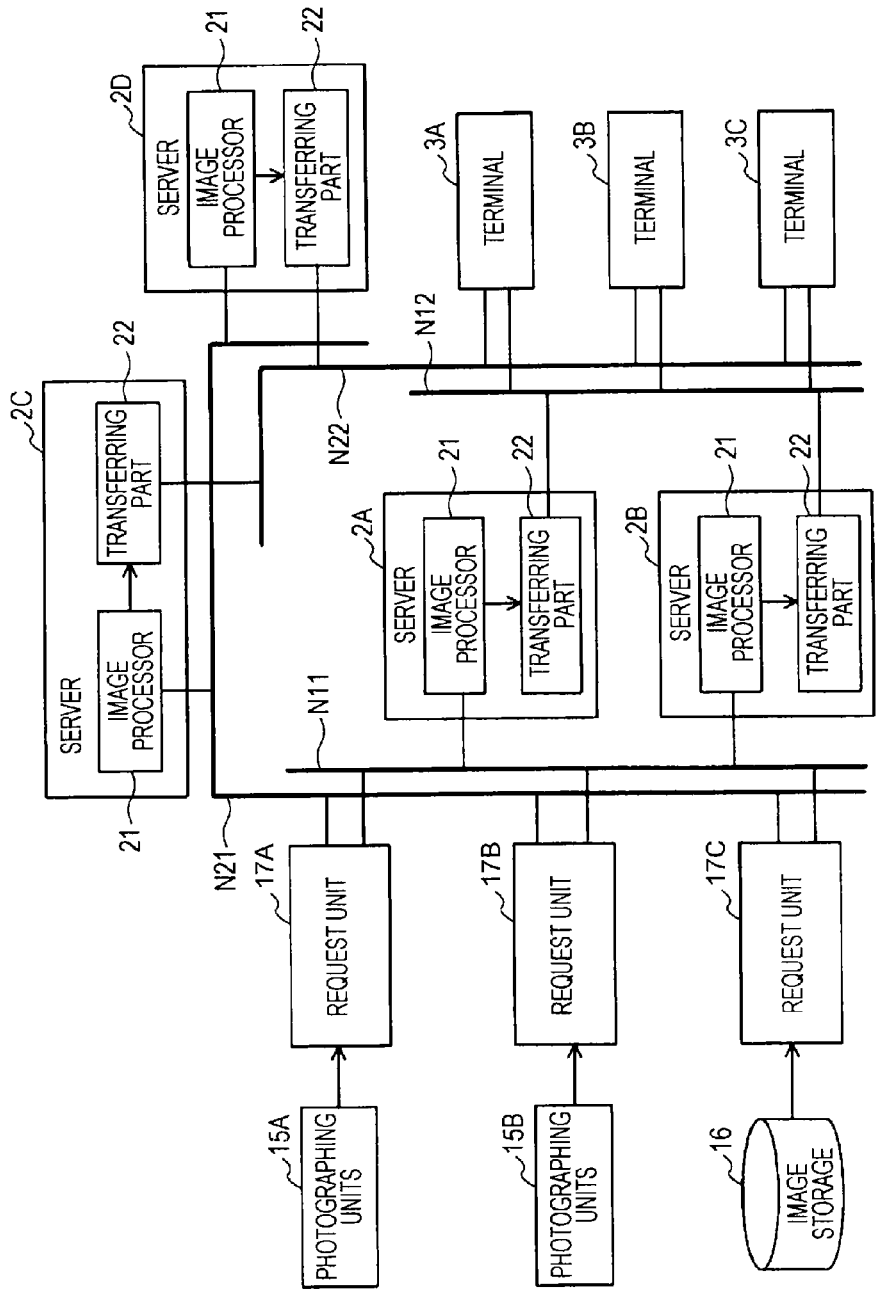
FIG. 3 is a block diagram of the medical image processing system focusing on the flow of processes with respect to the image data.

Here, FIG. 2 is referred. As illustrated in FIG. 2, the reservation manager 11 comprises a reservation receiving unit 111 and a processing condition specifying part 112.

(Reservation Receiving Unit 111)

The reservation receiving unit 111 receives test reservations related to capturing image data using modalities 15A or 15B from the operator. FIG. 4 is an example of a reservation management table TBL10 for the reservation receiving unit 111 to manage test reservations. As shown in FIG. 4, the test reservations managed and stored in the reservation management table TBL10 comprise, for example, a test identifier C11, an imaging part identifier C12, a test commencement time C13, a test termination time C14, an image processing category C15, an image size C16, number of images C17, and return destination C18 as information. The reservation receiving unit 111 receives the information as a reservation, and generates the reservation management table TBL10. The test identifier C11 is an identifier for identifying the test, and each test reservation is identified using the test identifier C11. The imaging part identifier C12 shows the identifier of the modality 15 that photographs the image data (for example, modality 15A or 15B). Moreover, the test commencement time C13 and the test termination time C14 show the time at which the test is commenced as well as the predicted termination time. The image processing category C15 is an identifier for identifying the categories of image processing with respect to the image data. Details on the image processing category C15 are mentioned later. An image size C16 shows the size of one image comprised in the image data, and the data volume of one image is specified by the size. The image size comprises information such as, for example, the number of colors in the image (bit number), the dimensions of the image (width and height of the image), etc. The number of images C17 shows the amount of image data. The total image data volume subject to image processing is specified by the image size C16 and the number of images C17. The return destination C18 shows the final output destination of the image data. For example, when displaying the photographed image data as an image, an identifier of the terminal (clients/workstations)

showing the image is input to the return destination C18. For example, "test a", or "examination/study a" indicates that the image data is photographed in modality 15A with times Ta1 to Ta2 as the testing times. Moreover, it shows that image processing shown by category M11 is carried out with respect to the amount of image data Na, with the size thereof defined by a condition P11.

Moreover, the reservation management table TBL10 may be configured allowing for both managing and storing the image processing reservation with respect to the image data photographed in advance and stored in the image storage 16. For example, test (study/examination) c relates to image processing of the image data stored in the image storage 16. In this case, the reservation receiving unit 111 receives the file name, image processing category C15, the process commencement time, and the process termination time of the image processing of the image data subject to image processing. In this case, it is not accompanied by photographing using the modality 15; therefore, the reservation receiving unit 111 does not input information on the imaging part identifier C12 during the test reservation of test (examination/study) c, and instead inputs the file name C19 for specifying the image data. Moreover, the reservation receiving unit 111 inputs the process commencement time and process termination time of the image processing to the test commencement time C13 and test termination time C14 instead of the commencement time and termination time of the examination (test). The image data subject to image processing is already stored in the image storage 16. Accordingly, the reservation receiving unit 111 specifies the image data from the image storage 16 based on the file name C19, reads the image size C16 and the number of images C17 from the specified image data, and inputs these to the reservation management table TBL10.

Next, the image processing category C15 is described with reference to FIG. 5. In the image processing with respect to the image data, various processes are carried out depending on the appearance of the output image. As an example, the reservation receiving unit 111 stores the image processing by category as information that has been classified in advance. Such classification should be carried out by the operator in advance. For example, FIG. 5 is an example of the management table TBL20 that manages correspondence between the image processing category C15 and the process carried out. Regarding the image data, the content of data and the content of the carried out image processing differs depending on the imaging part (specifically, the modality of the imaging part). Accordingly, the reservation receiving unit 111 manages and stores the correspondence for each image processing category C15 using the management table TBL20. Furthermore, the reservation receiving unit 111 allows the throughput calculator 12 and the analyzer 13, mentioned later, to refer to the management table TBL20. A configuration is also possible in which the storage storing the management table TBL20 is provided separately along with the reservation receiving unit 111, the throughput calculator 12, and the analyzer 13 referring to the storage.

As illustrated in FIG. 5, the management table TBL20 comprises an image processing classification C15, image classification C21, and processing content C22. The image classification C21 shows the image data classification (modality) subject to processing of the series of image processes shown in the image processing classification C15. Moreover, the processing content C22 shows the list of processes carried out. For example, the image processing of classification M11 with the image processing classification C15 shows that the image classification C21 will carry out process 1, process 2, and process 3 with respect to the MOD1 image data.

When the reservation management table TBL10 illustrated in FIG. 4 is generated, the reservation receiving unit 111 outputs the generated reservation management table TBL10 to the processing condition specifying part 112.

(Processing Condition Specifying Part 112)

The processing condition specifying part 112 receives the reservation management table TBL10 from the reservation receiving unit 111. The processing condition specifying part 112 calculates the image processing in each reserved test, that is, the commencement time C41 and process termination time C42 of the reserved image processing, based on the reservation management table TBL10 (the details thereof are described in a later paragraph). The processing condition specifying part 112 creates a process management table TBL40 for each server operating as the main server (that is, servers 2A and 2B) based on the process commencement time C41 and the process termination time C42. FIG. 7 is an example of the process management table TBL40 related to the image process reserved in server 2A. Furthermore, which among servers 2A to 2B the image processing for each reserved test should be divided into is determined in advance based on, for example, the image processing classification C15. For example, classifications M11, M12, M22, and M31, which are assigned in examinations (studies) a to d as the image processing classification C15, are associated with server 2A while others (for example, classification M21) are associated with server 2B. Moreover, it may be determined in advance based on the modality 15 capturing the image data. Hereinafter, the case of server 2A is explained as an example. Furthermore, the throughput C43 per unit time is calculated by the throughput calculator 12 mentioned later, which is then input into the process management table TBL40. The method for calculating the process commencement time C41 and the process termination time C42 are explained in detail in the following by dividing them into examination (test) a, which accompanies photographing of the image data, and examination (test) c, which does not accompany photographing of the image data.

First, examination (test) a, which accompanies photographing of the image data, is explained. When accompanied by photographing of the image data, at the time in which output of the image data photographed using the modality 15 is commenced, image processing with respect to the data may be commenced. Therefore, the processing condition specifying part 112 stores in advance the time T', which is from the modality 15 commencing photographing to commencing output of the image data, and calculates the time "Ta3" as the process commencement time C41 based on the time "Ta1" set for the test commencement time C13 and the time T'. Moreover, if the time T' differs depending on the data volume of the photographed image data, the time T' for each predetermined image volume should be stored in advance and the "Ta3" should be calculated as the process commencement time C41 together with the data volume of the photographed image data. Furthermore, the image data volume may be calculated based on the image size C16 and number of images C17 in the reservation management table TBL10.

Moreover, the processing condition specifying part 112 specifies the time "Ta4" as the process termination time C42 based on the time "Ta2" set to the test termination time C14. For example, if the image processing needs to be terminated before the test termination time "Ta2," the processing condition specifying part 112 specifies the time before the predetermined time "Ta4" from the test termination time "Ta2" as the process termination time C42. In addition, the time "Ta2"

may be specified as the process termination time C42. In addition, the time "Ta2" to the time "Ta4" following the predetermined time may be specified as the process termination time C42. In addition, the time from the process commencement time "Ta3" to the time following the predetermined processing time in the server "Ta4" may be specified as the processing time C42. The method for specifying the process termination time C42 should be appropriately set according to the requirements of the operating system.

Furthermore, in the case of examination (test) c, which does not accompany capturing the image data, the time Tc3 set to the test commencement time C13 corresponds to the process commencement time C41, while the time Tc4 set to the test termination time C14 corresponds to the process termination time C42.

The processing condition specifying part 112 generates the process management table TBL40 and inputs the process commencement time C41 and process termination time C42 regarding each examination (test), then outputs the process management table TBL40 to the throughput calculator 12 along with the reservation management table TBL10.

(Throughput Calculator 12)

The throughput calculator 12 receives the process management table TBL40 and reservation management table TBL10 from the processing condition specifying part 112. The throughput calculator 12 calculates the throughput C43 for each unit time (hereinafter, simply referred to as "throughput C43") based on the process commencement time C41 and process termination time C42 stored in the process management table TBL40 as well as the image size C16 and number of images C17 stored in the reservation management table TBL10. The method for calculating the throughput C43 is described in detail in the following.

First, the throughput calculator 12 specifies the data volume C32 per one image based on the image size C16. The data volume C32 per one image differs depending on the image classification C21, image size C16, and the process C31 with respect to the image. Accordingly, the throughput calculator 12 stores the correspondence as the management table TBL30. FIG. 6 illustrates an example of the management table. As illustrated in FIG. 6, the management table TBL30 stores the throughput C32 for each combination of the image classification C21, image size C16, and process C31. For example, a server with a predetermined processing capacity should be used to execute processing in advance regarding each combination, and the data volume should be calculated from the processing time at this time and the processing capacity of the server.

The throughput calculator 12 specifies the image classification C21 and processing content C22 from the management table TBL20 based on the image processing classification C15 stored in the reservation management table TBL10. Next, the throughput calculator 12 specifies the data volume C32 for each process included in the processing content C22 based on the image classification C21 and image size c16 with reference to the management table TBL30. For example, in the case of examination (test) a, the image classification C21 becomes "MOD1," the image size C16 becomes "condition P11," while the processing content C22 comprises "process 1," "process 2," and "process 3." As illustrated in FIG. 6, when the image classification C21 is "MOD1" and the image size C16 is "condition P11," the data volume C32 per one image of "process 1," "process 2," and "process 3" are "D111," "D112," and "D113." Accordingly, the throughput calculator 12 calculates the total data volume per one image as the sum of "D111," "D112," and "D113."

Next, the throughput calculator 12 calculates the total data volume for each test based on the calculated total data volume for each one image and the number of images C17 stored in the reservation management table TBL10. The throughput calculator 12 divides the total calculated data volume by the time width from the process commencement time C41 to the process termination time C42 stored in the process management table TBL40, to determine the data volume to be processed for each predetermined unit of time as the "throughput." The throughput calculator 12 inputs the calculated throughput to the throughput C43 of the process management table TBL40. For example, in the case of examination (test) a, the number of images C17 becomes "Na," the process commencement time C41 becomes "Ta3," the process termination time C42 becomes "Ta4," and the throughput C43 becomes "Da." Furthermore, when the time width of the unit time is considered "T0," Da=(D111+D112+D113)×Na×T0/(Ta4−Ta3).

Furthermore, some image processes require a constant processing time regardless of the data volume. In this case, the throughput C43 should be calculated taking the time into consideration. For example, process 2 requires a constant processing time T2 in addition to processing with respect to the data volume D112. In this case, the throughput Da in examination (test) a shown in the preceding example should be calculated based on the time width in which the processing time T2 is subtracted from the time width (Ta4-Ta3). That is, it becomes Da=(D111+D112+D113)×Na×T0/(Ta4−Ta3−T2).

The throughput calculator 12 outputs the process management table TBL40 and the reservation management table TBL10 input with the throughput C43 to the analyzer 13.

(Analyzer 13)

The analyzer 13 comprises the request processing specifying part 131, request destination specifying part 132, and request information manufacturer 133. The analyzer 13 receives the process management table TBL40 and reservation management table TBL10 from the throughput calculator 12 and outputs these to the request processing specifying part 131.

(Request Processing Specifying Part 131)

Figure 8:
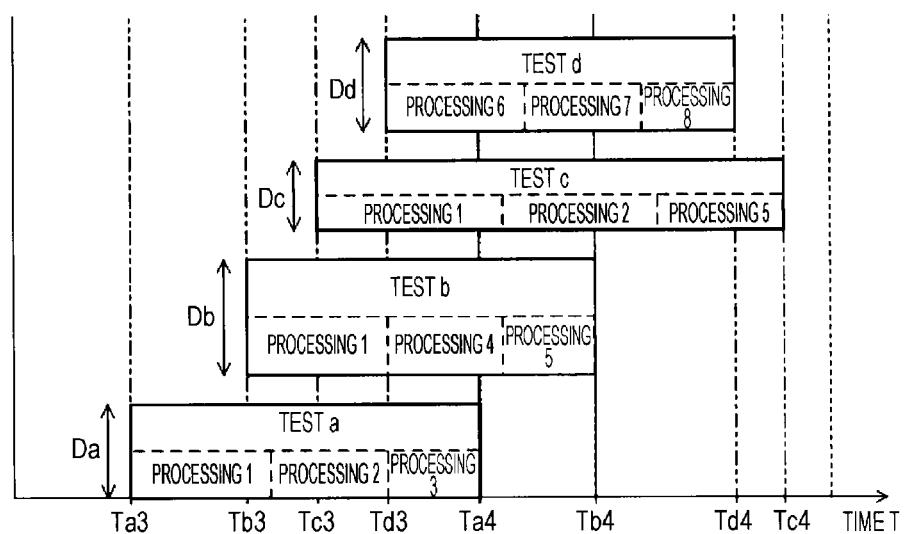
FIG. 8 is an example of the processing schedule of the image processing pertaining to Embodiment 1.

The request processing specifying part 131 receives the process management table TBL40 and creates a processing schedule of image processing for each test carried out in server 2A based on the process commencement time C41 and process termination time C42 stored in the process management table TBL40. FIG. 8 is an example of the processing schedule of the image processing carried out in server 2A created based on the process management table TBL40. Furthermore, at this time, the request processing specifying part 131 associates the throughput C43 with the schedule of each test, as illustrated in FIG. 8.

Figure 9A:
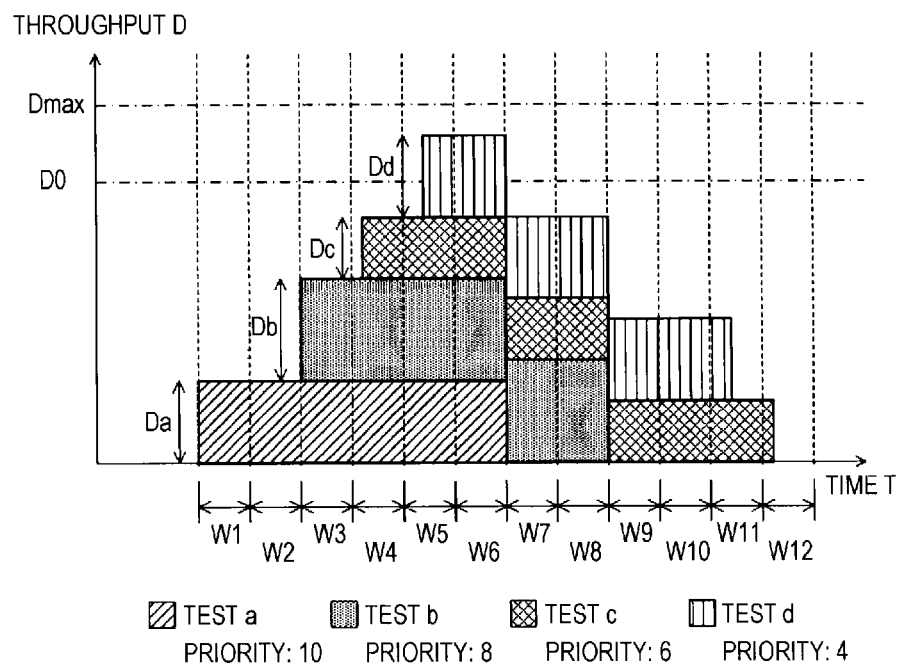
FIG. 9A is an example of load prediction data.

The request processing specifying part 131 adds the throughput C43 of each image process carried out in server 2A for each predetermined time width to create load predicting data. FIG. 9A is an example of the load predicting data. Next, the request processing specifying part 131 determines whether or not the total D of the throughput C43 of each image process becomes the predetermined throughput D0 or more. FIG. 9A is an example of when a period from the image process commencement time "Ta3" of examination (test) a, which is commenced earliest, to the image process termination time of examination (test) c, which terminates last, is divided into time widths W1 to W12 using a unit time width determined in advance. Furthermore, the predetermined throughput D0 is determined in advance within a range not exceeding the maximum throughput Dmax of the server as the maximum allowable processing load.

For example, in FIG. 9A, the total D of the throughput C43 of the image processing carried out in the time width W3 becomes D=Da+Db<D0. Moreover, the total D of the throughput C43 of the image processing carried out in the time width W6 becomes D=Da+Db+Dc+Dd≥D0. In this manner, the request processing specifying part 131 calculates the total D of the throughput C43 for each time width, and compares it with the predetermined throughput D0. In the example of FIG. 9A, the total throughput C43 becomes the predetermined throughput D0 or more in the time widths W5 and W6.

Figure 9B:
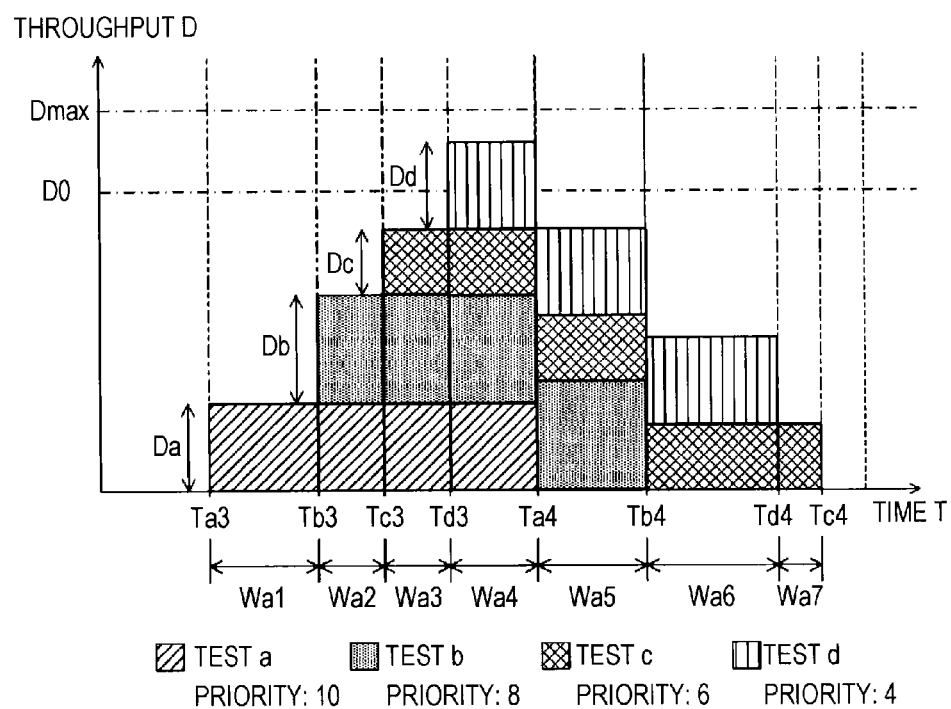
FIG. 9B is an example of load prediction data.

Furthermore, there is no need to be necessarily divided by the unit time width determined in advance. For example, as shown in FIG. 9B, the time width may be divided at a timing in which the combination of the image processing carried out in parallel changes. In this case, as shown in FIG. 9B, the time width between Ta3 to Tc4 is divided at the points of the time at which image processing is commenced Tb3, Tc3, and Td3 as well as the time at which image processing is terminated Ta4, Tb4, and Td4, to obtain the time widths shown with Wa1 to Wa7, which are respectively determined as the time width. For example, in the time width Wa1, only the image processing of "examination (test) a" is carried out. Moreover, in the time width Wa4, each imaging process of examinations (studies) a to d are carried out in parallel, so that the total D of the throughput C43 at this time becomes the predetermined throughput D0 or more.

When the total throughput C43 is the predetermined throughput D0 or more, the request processing specifying part 131 specifies the image processing to request substitution of the supporting server (that is, server 2C or 2D) from among the image processes in which execution is scheduled at the time width thereof. At this time, by means of weighing the priority prior to each test, the request processing specifying part 131 is capable of specifying the image process with the least priority as the image process to request the processing thereof to the supporting server (hereinafter, this may be referred to as "requested image process"). Furthermore, the weighing of priority for each test may be set such that priority is given when accepting requests, or it may be set in advance for each image processing classification C15. The request processing specifying part 131 specifies the requested image process until the total throughput C43 becomes less than the predetermined throughput D0.

For example, in the case of FIG. 9A, the total D of the throughput C43 becomes the predetermined throughput D0 or more in the time widths W5 and W6. Accordingly, the request processing specifying part 131 compares the priorities of the image processes of examinations (studies) a to d, to specify the image processing of examination (test) d, which has the lowest priority, as the requested image process.

Once the image process to request substitution to the supporting server has been specified, the request processing specifying part 131 transmits the process management table TBL40 and reservation management table TBL10 to the request destination specifying part 132. At this time, the request processing specifying part 131 notifies the request destination specifying part 132 of the specified requested image process which is to be requested to the supporting server (in the case of FIG. 9A, the image processing of examination (test) d) together.

(Request Destination Specifying Part 132)

The request destination specifying part 132 receives the process management table TBL40 and reservation management table TBL10 as well as the notification of the requested image process. The request destination specifying part 132 specifies any one from among servers 2C and 2D operating as the supporting server as the server to request the notified image processing. At this time, the request destination specifying part 132 should, for example, associate in advance the supporting server of the request destination (hereinafter, simply referred to as the "request destination") for each main server which is the origin of execution. Moreover, the request destination specifying part 132 may set in advance the request destination for each image processing classification C15 of the notified image. In this case, the request destination specifying part 132 refers to the reservation management table TBL10 to specify the image processing classification of the notified image processing. Hereinafter, the request destination specifying part 132 is described assuming that server 2C has been specified as the request destination of the image processing of examination (test) d.

The request destination specifying part 132 associates the specified request destination (server 2C) with notified requested image process (image processing of examination (test) d), and the return destination C18 of the image data as one group. Furthermore, when there are a plurality of requested image processes, the request destination specifying part 132 specifies the request destination for each of the requested image processes, and associates them as request information. The request destination specifying part 132 outputs the created group, the process management table TBL40, and reservation management table TBL10 to the request information manufacturer 133.

As mentioned above, regarding all time widths, the request processing specifying part 131 and request destination specifying part 132 calculates the total D of the throughput C43, compares the total D with the predetermined throughput D0, and specifies the requested image process and request destination when the total D becomes the throughput D0 or more.

(Request Information Manufacturer 133)

The request information manufacturer 133 receives the group to which the request destination, requested image process, and return destination C18 are associated from the request destination specifying part 132, further receiving the process management table TBL40 and the reservation management table TBL10 therefrom.

Figure 10:
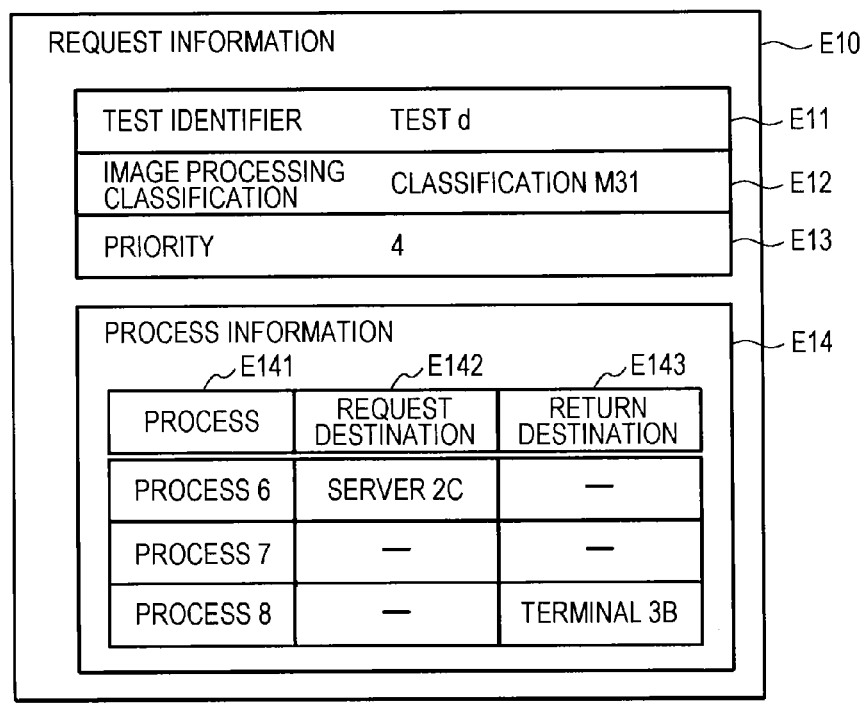
FIG. 10 illustrates an example of the data configuration of request information pertaining to Embodiment 1.

The request information manufacturer 133 generates request information E10 for each test stored in the reservation management table TBL10. FIG. 10 is an example of the data configuration of the request information E10. The request information E10 comprises a test identifier E11, a test classification E12, a priority E13, and process information E14. The request information manufacturer 133 inputs the test identifier C11 stored in the reservation management table TBL10 and the information stored in the image processing classification C15 to the test identifier E11 and image processing classification E12. Moreover, the request information manufacturer 133 inputs the priority set in advance with respect to the test to the priority E13.

Moreover, with the process E141, request destination E142, and return destination E143 as one group, the process information E14 is provided for each process in which the group configures image processing. For example, the image process classification of examination (test) d is classification M31, and "process 6," "process 7," and "process 8" are carried out in this order as the processing content of the image processing. Accordingly, the information showing "process 6," "process 7" and "process 8" are input into the processing information E14 in this order. The request destination E142 shows the request destination to request the execution of the corresponding process. Moreover, the return destination E143 shows the return destination to which the image data is returned following the process.

The method for setting the request destination E142 is variable depending on the examination (test) in which image processing is carried out in the main server and the examination (test) in which image processing is requested to the supporting server. The request destination specifying part 132 notifies the request information manufacturer 133 of the image processing requested to the supporting server as the group of the request destination and the requested image processing. Accordingly, the request information manufacturer 133 compares this notified group with the reservation management table TBL10, to divide the examination (test) for image processing in the main server from the examination (test) for requesting the image processing to the supporting server.

Regarding the examination (test) in which image processing is requested to the supporting server, the request information manufacturer 133 inputs information on the request destination included in the notified group as the request destination E142. For example, it is configured such that image processing of examination (test) d is requested to server 2C by means of the group notified by the request destination specifying part 132. That is, it is indicated that the series of processes "process 6," "process 7" and "process 8" configuring the image processing of examination (test) d are requested to server 2C. Accordingly, the request information manufacturer 133 sets "server 2C" to the request destination E142 of "process 6," which is carried out first from among the series of processes. Moreover, the reservation management table TBL10 has a return destination C18 for transmitting examination (test) d to "terminal (clients/workstations) 3B" following completion of the series of processes. Accordingly, the request information manufacturer 133 determines "terminal (clients/workstations) 3B" as the return destination E143 of "process 8" to be finally carried out in the series of processes. Furthermore, the request information manufacturer 133 inputs, for example, a "-(blank)" as the information indicating that information is not input to other request destinations E142 and return destination E143. Furthermore, in the example of FIG. 10, "process 6," "process 7," and "process 8" may be respectively carried out in different servers. The example in this case is mentioned later as Modified Example 1.

Moreover, the information showing the main server is associated with the process management table TBL40. Accordingly, regarding examinations (studies) in which image processing is carried out by the main server (for example, examinations (studies) a to c), the request information manufacturer 133 sets the information showing the main server, that is, the information showing "server 2A" to the request destination E142. Furthermore, the method for setting the return destination E143 is the same as in the examination (test) d.

The request information manufacturer 133 outputs the request information on each test, the process management table TBL40, and reservation management table TBL10 to the process controller 14.

(Process Controller 14)

The process controller 14 receives the request information on each test, the process management table TBL40, and reservation management table TBL10 from the request information manufacturer 133. The process controls unit 14 controls the operation of the request unit 17 and servers 2A to 2D based on the information. Furthermore, the request unit 17 is associated and set in each modality 15 and image storage 16.

Furthermore, details on the request unit 17 are described later. Details on the process controller 14 are described in the following.

The process controller 14 specifies the commencement time of each test with the reservation management table TBL10 as a reference. The process controller 14 instructs the commencement of photographing to modalities 15A and 15B according to the specified test commencement time.

Moreover, the process controller 14 specifies the request unit 17 in which the image process for each test is output based on the reservation management table TBL10. For example, as illustrated in FIG. 4, the image data is photographed in modality 15B regarding examination (test) d. Accordingly, the process controller 14 specifies the request unit 17 associated and set to modality 15B.

Moreover, the process controller 14 specifies the time at which the image processing of each test commences with reference to process management table TBL40. The process controller 14 notifies the corresponding request unit 17 of the request information on each test in advance before the image process of the test is commenced.

Moreover, as in examination (test) c, regarding reservation of the image processing with respect to the image data stored in the image storage 16, the process controller 14 notifies the corresponding request unit 17 of the file name C19 of the image data subject to image processing along with the request information. In response to the notification, the request unit 17 reads out the corresponding image data based on the notified file name C19 from the image storage 16.

Next, the process controller 14 specifies the process commencement time C41 of each image processing with reference to the process management table TBL40. Moreover, the process controller specifies the server executing the image processing of a examination (test) based on the request information for each test. For example, FIG. 7 is a process management table TBL40 of server 2A, and from within this table, the image processing of examination (test) d is requested to server 2C. In this case, the request information on examinations (studies) a to c comprises information indicating server 2A as the processing information E14. In the same manner, the request information on examination (test) d comprises information indicating server 2C as the processing information E14. Accordingly, the process controller 14 instructs the server 2A to carry out image processing of examinations (studies) a to c based on the process commencement time C41. Moreover, the process controller 14 instructs server 2C to carry out image processing of examination (test) d.

As mentioned above, the operations of modalities 15A and 15B, each request unit 17, and servers 2A to 2D are controlled by means of the operation of the reservation manager 11, throughput calculator 12, analyzer 13, and the process controller 14.

Next, configurations of the request unit 17 and servers 2A to 2D are described with reference to FIG. 1 and FIG. 3. FIG. 3 is a block diagram focusing on the flow from the image data photographed in modalities 15A to 15B and the image data stored in the image storage 16 undergoing image processes by means of any one from among servers 2A to 2D until it is output to the terminal (clients/workstations) 3.

(Request Unit 17)

The request unit 17 is associated with the modality 15 and the image storage 16, respectively, and set.

The request unit 17 associated with the modality 15 receives the photographed image data from the modality 15. Moreover, the request unit 17 receives request information from the process controller 14.

Figure 11:
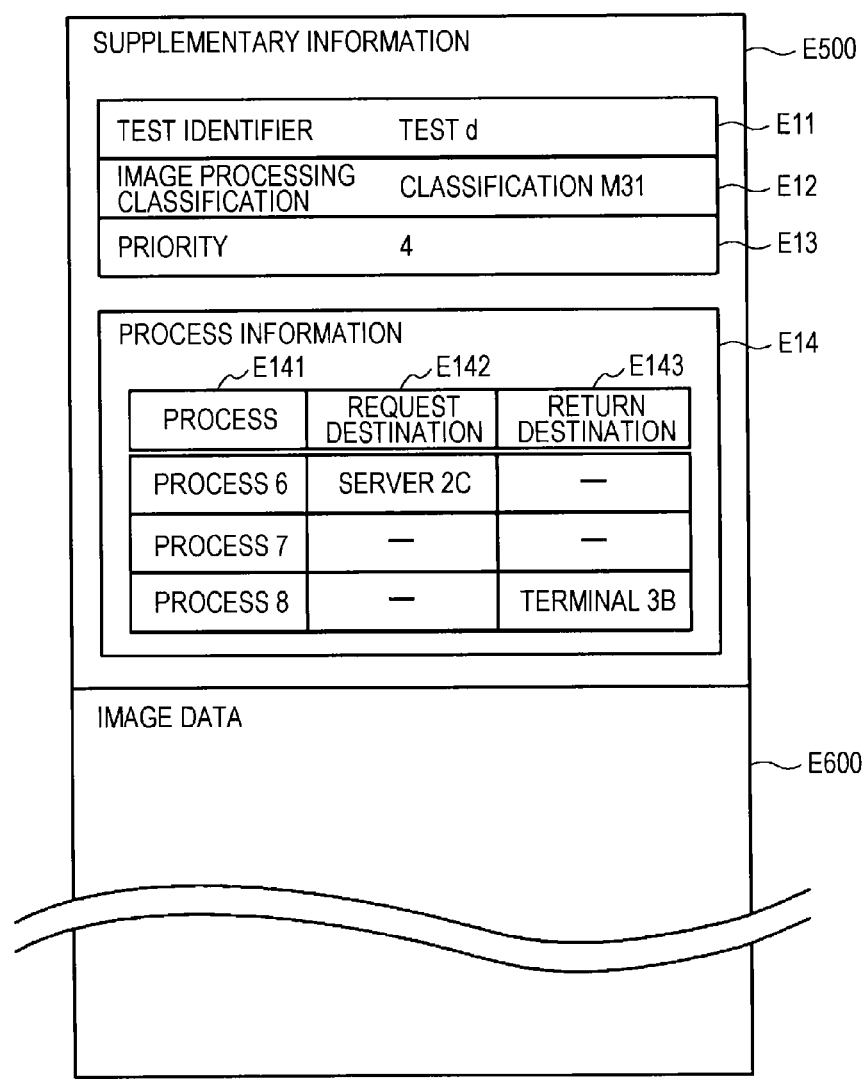
FIG. 11 is an example of data configuration of the image data related to the present embodiment.

The request unit 17 reads out the test identifier E11, test classification E12, priority E13, and processing information E14 from the received request information and supplements these to the image data received from the modality 15. FIG. 11 is an example of the data configuration related to the present embodiment. As illustrated in FIG. 11, the image data comprises supplementary information E500 and actual image data E600. The actual image data E600 is the data that becomes the origin for manufacturing the image. The supplementary information E500 comprises information showing the attributes of the image data thereof. The test identifier E11, test classification E12, priority E13, and processing information E14 read from the request information are, as illustrated in FIG. 11, input into the supplementary information E500.

The request unit 17 reads the information regarding the request destination E142 of the information on the first process from among the information on each process included in the processing information E14, and specifies server 2 transmitting the image data. For example, in FIG. 11, the request destination E142 of the first defined "process 6" of the processing information E14 is read and "server 2C" is specified. The request unit 17 transmits image data to the specified server 2C.

Moreover, the request unit 17 associated with the image storage 16 receives the file name C19 of the image data subject for image processing as the request information from the process controller 14. The request unit 17 reads out the image data corresponding to the file name C19 from the image storage 16.

Moreover, the request unit 17 reads the test identifier E11, test classification E12, priority E13, and processing information E14 from the received request information, and supplements these to the image data read from the image storage 16. The processes hereinafter are the same as the request unit 17 associated with the modality 15.

Furthermore, each request unit 17 may be associated with the modality 15 and the image storage 16, respectively, and operated together as one request unit 17.

Next, the configuration of servers 2A to 2D is described with an example in which the image data related to examination (test) d illustrated in FIG. 11 is processed in server 2C.

Server 2C comprises the image processor 21 and a transferring part 22.

The image processor 21 receives the image data from the request unit 17. Moreover, the image processor 21 instructs the execution of image processing from the process controller 14.

When execution of image processing is instructed, the image processor 21 first reads the processing information E14 supplemented to the image data received from the request unit 17. Next, the request destinations E142 registered in the processing information E14 for each process are successively read. In the process, the image processor 21 specifies the first row of the request destination E142 comprising the information showing the request destination. In the case of FIG. 11, the image processor 21 of server 2C specifies the row of "process 6" in which "server 2C" is set in the request destination E142 as the first row.

Next, the image processor 21 successively reads the process E141, the request destination E142, and the return destination E143 in order from the first row and carries out the process setup to the process E141 of the read row. The image processor 21 carries out the process until it reads out the second row in which information is input to the return destination E143 (that is, information set other than the "-(blank)"). In the case of FIG. 11, "-(blank)" is setup regarding the return destination E143 of the "process 6" and "process 7" rows, while "terminal (clients/workstations) 3B" is set to the return destination E143 of "process 8." Accordingly, the image processor 21 operates "process 6," "process 7," and "process 8" in this order.

When the second row is read, the process setup in process E141 is carried out, after which, the image data that underwent the process as well as the return destination E143 is output to the transferring part 22. In the case of FIG. 11, the image processor 21 carries out "process 8" and subsequently notifies the transferring part 22 of the image data after "process 8" and "terminal (clients/workstations) 3B" set to the return destination E143.

The transferring part 22 receives the processed image data and the destination E143 from the image processor 21. The transferring part 22 transmits the received image data to the address indicated in the return destination E143. That is, in case of the example illustrated in FIG. 11, the transferring part 22 transfers the image data of examination (test) d to "terminal (clients/workstations) 3B" after "process 6," "process 7," and "process 8" have been carried out in the image processor 21 of server 2C.

Furthermore, in the abovementioned, the trigger at which the image processor 21 of servers 2A to 2D commences image processing is not necessarily limited to the instruction of the process controller 14. For example, when the image processor 21 receives the image data from the request unit 17, image processing may be commenced with the transmission as the trigger. In this case, the process controller 14 is not required to instruct commencement of image processing to each server.

Figure 12:
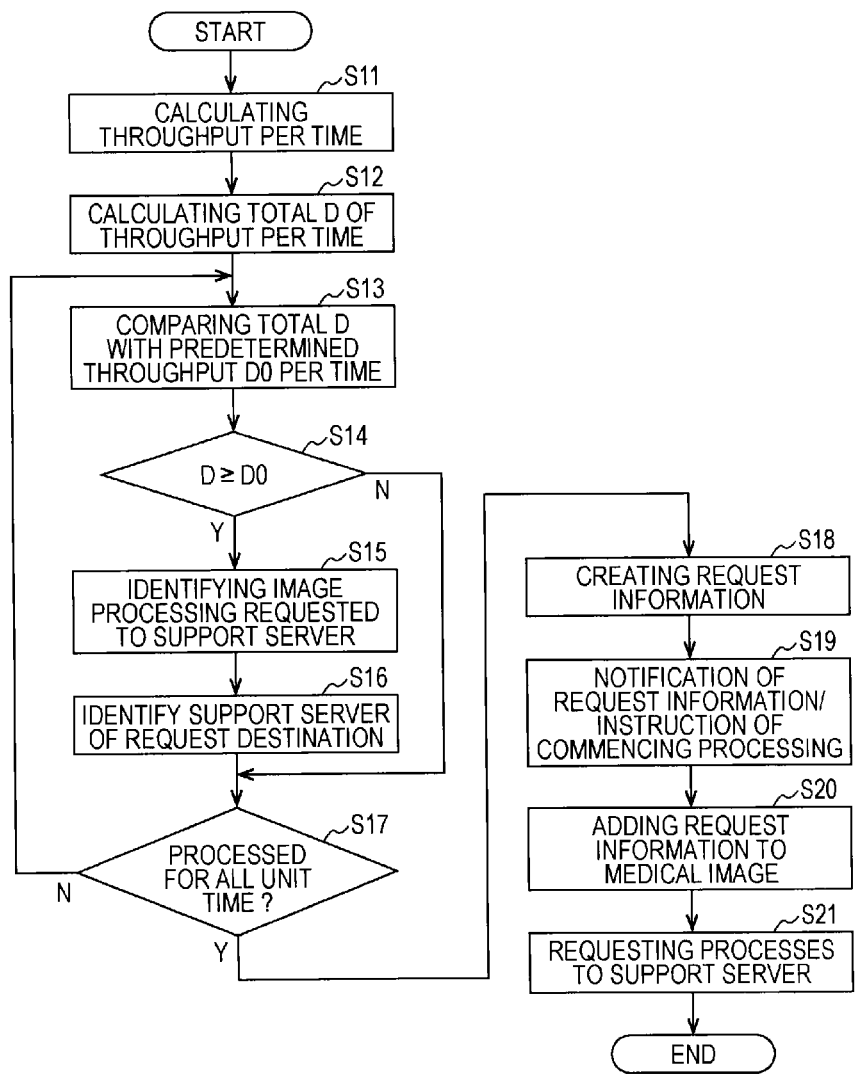
FIG. 12 is a flow chart illustrating the series of actions from specifying the image process to request the supporting server until requesting the image process.

Next, the operation of the analyzer 13 is described with reference to FIG. 12. FIG. 12 is a flow chart showing the series of actions from specifying the image processing to request the supporting server until requesting the image processing.

(Step S11)

The reservation receiving unit 111 receives test reservations related to image data photographing using modality 15A or 15B, and generates the reservation management table TBL10 as illustrated in FIG. 4. The reservation receiving unit 111 outputs the generated reservation management table TBL10 to the processing condition specifying part 112.

The processing condition specifying part 112 receives the reservation management table TBL10 from the reservation receiving unit 111. The processing condition specifying part 112 calculates the image processing in each reserved test, that is, the process commencement time C41 and process termination time C42 of the reserved image processing based on the reservation management table TBL10. The processing condition specifying part 112 generates the process management table TBL40 based on the process commencement time C41 and the process termination time C42. The processing condition specifying part 112 outputs the generated process management table TBL40 to the throughput calculator 12 together with the reservation management table TBL10.

The throughput calculator 12 receives the process management table TBL40 and reservation management table TBL10 from the processing condition specifying part 112. The throughput calculator 12 specifies the data volume C32 for each image based on the image size C16. The throughput calculator 12 specifies the image classification C21 and processing content C22 from the management table TBL20 based on the image processing classification C15 stored in the reservation management table TBL10. Next, the throughput calculator 12 specifies the data volume C32 for each process comprised in the processing content C22 based on the image classification C21 and image size C16 with reference to the management table TBL30.

Next, the throughput calculator 12 calculates the total data volume based on the calculated total data volume for each image and the number of images C17 stored in the reservation management table TBL10. The throughput calculator 12 divides the calculated total data volume by the time width from the predetermined process commencement time C41 to the process termination time C42, thereby calculating an amount of data to be processed for each predetermined unit time as the throughput C43, and inputs this into the process management table TBL40.

The throughput calculator 12 outputs the process management table TBL40 with the throughput C43 input and the reservation management table TBL10 to the analyzer 13.

(Step S12)

The analyzer 13 receives the process management table TBL40 and reservation management table TBL10 from the throughput calculator 12, and outputs these to the request processing specifying part 131.

The request processing specifying part 131 receives the process management table TBL40 and generates an image processing schedule for each test carried out in server 2A, as shown in FIG. 8, based on the process commencement time C41 and process termination time C42 stored in the process management table TBL40.

The request processing specifying part 131 respectively adds the throughput C43 of each image processing carried out in server 2A for each time width to generate the load predicting data such as those illustrated in FIG. 9A.

(Step S13)

Next, the request processing specifying part 131 calculates the total D of the throughput C43 for each time width, for comparison with the predetermined throughput D0. By means of the comparison, the request processing specifying part 131 determines whether the total D of the throughput C43 for each image processing time width becomes the predetermined throughput D0 or more. Furthermore, the predetermined throughput D0 is set in advance as the maximum allowable processing load within a range not exceeding the maximum throughput Dmax of the server.

(Step S15)

When the total D of the throughput C43 becomes the predetermined throughput D0 or more (step S14, Y), the request processing specifying part 131 specifies the image process for a request of substitution to the supporting server from among the image processes in which execution is scheduled at the time width. The request processing specifying part 131 specifies the request image processing until the total throughput C43 becomes less than the predetermined throughput D0.

Once the image process to request substitution of the supporting server has been specified, the request processing specifying part 131 transmits the process management table TBL40 and reservation management table TBL10 to the request destination specifying part 132. At this time, the request processing specifying part 131 notifies the request destination specifying part 132 of the specified requested image process to request the supporting server (in the case of FIG. 9A, the image processing of examination (test) d) along with this.

(Step S16)

The request destination specifying part 132 receives notification of the process management table TBL40 and reservation management table TBL10 and the requested image processing. The request destination specifying part 132 specifies one from among servers 2C and 2D, which operate as supporting servers, as the server to request the notified image processing. At this time, the request destination specifying part 132 should be, for example, associated in advance with the request destination for each main server of the origin of execution. Moreover, the request destination specifying part 132 may set the request destination in advance for each image processing classification C15 of the notified image processing. In this case, the request destination specifying part 132 refers to the reservation management table TBL10 and specifies the image processing classification C15 of the notified image processing.

Furthermore, when the total D of the throughput C43 does not become the predetermined throughput D0 or more (step S14, N), it transits to the next process without carrying out the processes shown in steps S15 and 16.

(Step S17)

The request processes specifying part 131 and request destination specifying part 132 carries out the processes related to the steps S13 to S16 regarding the next time width when processes are not completed regarding all time widths (step S17, N).

(Step S18)

When processes are completed regarding all time widths (step S17, Y), the request information manufacturer 133 generates the requested information E10 illustrated in FIG. 10 for each test stored in the reservation management table TBL10. The request information manufacturer 133 inputs the test identifier C10 stored in the reservation management table TBL10 and the information stored in the image processing classification C15 into the test identifier E11 and the image processing classification E12. Moreover, the request information manufacturer 133 inputs into the priority E13 the priority set in advance into the test priority E13. Moreover, with the process E141, request destination 142, and return destination E143 as one group, the request information manufacturer 133 generates the request information for each process in which the group configures the image processing, and outputs this to the processing information E14. Furthermore, the request information manufacturer 133 compares the notified group with the reservation management table TBL10, and divides them into a examination (test) in which image processing is carried out in the main server and a examination (test) in which image processing is requested to the supporting server. Regarding the examination (test) in which image processing is requested to the supporting server, the request information manufacturer 133 inputs the information on the request destination comprised in the notified group as the request destination E142. Regarding examinations (studies) in which image processing is carried out in the main server (for example, examinations (studies) a to c), the request information manufacturer 133 sets the information showing the main server to the request destination E142.

The request information manufacturer 133 outputs the request information on each test, the process management table TBL40 and reservation management table TBL10 to the process controller 14.

(Step S19)

The process controller 14 specifies the test commencement time of each test with reference to the reservation management table TBL10. The process controller 14 instructs modalities 15A and 15B to commence photographing based on the specified test commencement time.

The process controller 14 specifies the request unit 17 in which the image processing for each test is output based on the reservation management table TBL10.

The process controller 14 specifies the time for commencing the image processing of each test with reference to the process commencement time C41 of the process management table TBL40. The process controller 14 notifies the corresponding request unit 17 of the requested information on each test in advance before the image processing of the test is commenced.

(Step S20)

The request unit 17 receives the photographed image data from the modality 15. Moreover, the request unit 17 receives the requested information from the process controller 14. The request unit 17 reads the test identifier E11, test classification E12, priority E13, and processing information E14 from the received requested information, and adds them to the image data received from the modality 15.

(Step S21)

The request unit 17 reads the information on the request destination E142 of the information on the first process from among the information on each process comprised in the processing information E14, and specifies server 2C transmitting the image data. The request unit 17 transmits image data to the specified server 2C.

As mentioned above, in the medical image processing system related to the present embodiment, the total throughput D for each time width regarding the reserved image processing is calculated for each main server carrying out image processing. On this basis, the total calculated throughput D is compared with the predetermined throughput D0, and when the total D becomes the throughput D0 or more, execution of some of the image processing scheduled to be carried out at the time width is requested to the supporting server. By means of taking such a configuration, it becomes possible to specify the period of time at which the processing load temporarily increases (that is, the period of time at which the load unsteadily increases), the image processing carried out in the period of time, and some specified image processing may be requested to the supporting server. The supporting server is not required to carry out steady image processing as with the main server. Accordingly, the server carrying out processes other than image processing may be temporarily operated as a supporting server or it becomes possible to provide the supporting server provided on an external system. Thereby, correspondence to the non-steady load becomes possible without having to install more main servers.

(Modified Example 1)

Next, the medical image processing system related to Modified Example 1 is described as a modified example of Embodiment 1. For example, image processing of examination (test) d comprises "process 6," "process 7," and "process 8" as the processing content. In the medical image processing system related to Embodiment 1, the request destination of the image processing was specified for each test. The medical image processing system related to Modified Example 1 is configured such that the request destination may be set for each process configuring image processing for each test. Hereinafter, the medical image processing system related to Modified Example 1 is described focusing on the operation of the analyzer 13 that is different from Embodiment 1.

The operations of the request processing specifying part 131 are the same as in Embodiment 1. Furthermore, hereinafter, descriptions are given assuming that the image processing of examination (test) d was specified as the requested image processing, in the same manner as Embodiment 1.

The request destination specifying part 132 related to Modified Example 1 stores in advance the function management table managing processing that may be carried out by each supporting server (that is, servers 2C and 2D). FIG. 14 is an example of the function management table. As illustrated in FIG. 14, the function management table comprises the server identifier C51 and an executable processing classification C52. The server identifier C51 is an identifier for distinguishing respective supporting servers. Moreover, the executable processing classification C52 indicates a series of processes executable in the supporting server indicated by the server identifier C51.

For example, in the example of FIG. 14, server 2C shows that "process 1," "process 2," "process 5," and "process 6" are executable. In the same manner, server 2D shows that "process 3," "process 4," "process 7," and "process 8" are executable. In the case of such a configuration, for example, it is impossible to carry out the image processing of examination (test) d, that is, "process 6," "process 7," and "process 8," with server 2C alone. Accordingly, the request destination specifying part 132 specifies the request destination for each process configuring image processing.

First, the request destination specifying part 132 specifies the processing content of the image processing of examination (test) d based on the management table TBL20 illustrated in FIG. 5. Thereby, "process 6," "process 7," and "process 8" are specified as the processing content of the image processing of examination (test) d.

Next, the request destination specifying part 132 specifies the supporting server capable of carrying out the process for each specified process. In the case of the configuration illustrated in FIG. 14, the request destination specifying part 132 specifies "server 2C" as the request destination of "process 6," and specifies "server 2D" as the request destination of "process 7" and "process 8." The request destination specifying part 132 associates each process with the request destinations specified regarding each process to be a pair and associates the respective pairs with the return destination C18 of the image data to be one group. The request destination specifying part 132 outputs the manufactured group, the process management table TBL 40 and reservation management table TBL10 to the request information manufacturer 133.

(Request Information Manufacturer 133)

Figure 13:
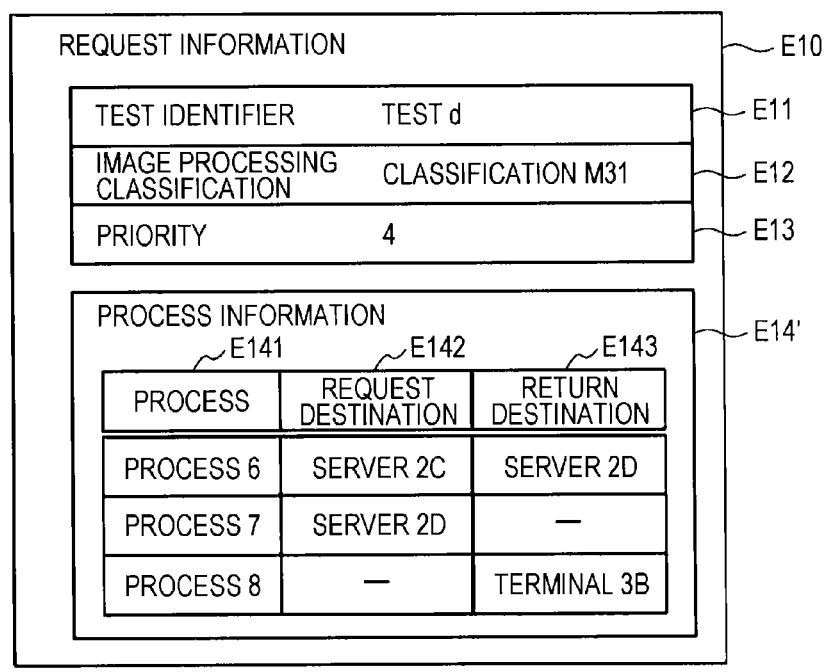
FIG. 13 is an example of data configuration of the request information pertaining to Modified Example 1.

The request information manufacturer 133 generates the requested information E10 for each test stored in the reservation management table TBL10. FIG. 13 illustrates a data configuration of the requested information E10 of examination (test) d regarding the example mentioned above. The data configuration of the requested information E10 is the same as the data configuration of the requested information E10 related to Embodiment 1; however, the content set in the processing information E14 differs. Here, a description is provided focusing on the method for generating the processing information E14'.

The request information manufacturer 133 confirms the request destination of each process configuring image processing of examination (test) d in the order in which they are executed. "Server 2C" is set to the request destination of "process 6," which is executed first. Accordingly, the request information manufacturer 133 inputs "process 6" to process E141 in addition to inputting "server 2C" to the request destination E142 of "process 6."

Next, the request information manufacturer 133 confirms the request destination of "process 7" executed following "process 6." The request destination of "process 7" is "server 2D," which is different from "process 6." Accordingly, the request information manufacturer 133 first inputs the next process, that is, the information on "server 2D," which is the request destination of "process 7," to the return destination E143 of the row of "process 6." Thereby, the image data is transmitted to "server 2D" when "process 6" is carried out in server 2C. Moreover, the request information manufacturer 133 inputs "process 7" into the process E141, generating the row of "process 7," while inputting "server 2D" into the request destination E142 of this row. Thereby, in "server 2D," processes are carried out starting with "process 7."

Next, the request information manufacturer 133 confirms the request destination of "process 8," which is carried out following "process 7." The request destination of "process 8" is "server 2D," which is the same as "process 7." Accordingly, the request information manufacturer 133 does not input information into the return destination E143 of the row of "process 7," and leaves it "-(blank)". Moreover, the request information manufacturer 133 inputs "process 8" to process E141, generating the row of "process 8." At this time, information is not input into the request destination E142 of the row of "process 8," and is left "-(blank)."

Furthermore, processes are not carried out following "process 8" onwards. Accordingly, the request information manufacturer 133 sets a "terminal (clients/workstations) 3B" set at the return destination C18 to the return destination E143 of the row of "process 8." Thereby, the image data is transmitted to "terminal (clients/workstations) 3B" after "process 8" has been carried out in "server 2D."

The processes hereinafter are the same as the medical image processing system related to Embodiment 1.

Furthermore, in the abovementioned, the supporting server alone was set as the request destination of processes; however, a configuration is possible including the main server in the request destination of some processes. For example, the total processing load D for each time width and the predetermined throughput D0 may be compared for each process configuring image processing, and not for each test. By means of operating in this manner, execution of only some processes from among each process configuring image processing may be requested to the supporting server, and the processes thereinafter can be taken over by the main server following the execution of the process. Furthermore, when transferring processing between the supporting server and the main server, the supporting server and the main server are connected via a network.

As mentioned above, in the medical image processing system pertaining to Modified Example 1, request destinations are set for each process configuring the image processing of each test, and these are supplemented to the image data as processing information E14'. Thereby, even when the executable process is different for each supporting server, image processing for each test may be carried out throughout a plurality of supporting servers. Thereby, there is no need for each supporting server to be capable of executing all processes, and the amount of software to install in each supporting server may be reduced. Accordingly, the time and effort taken for constructing each supporting server may be reduced and the amount of software to be used is limited; therefore, the remaining storage area may be used as the region for data.

(Embodiment 2)

Next, regarding Embodiment 2, the operation of the medical image processing system when new reservations are added is explained with reference to FIG. 15 to FIG. 18 focusing on parts that are different from Embodiment 1.

Figure 15:
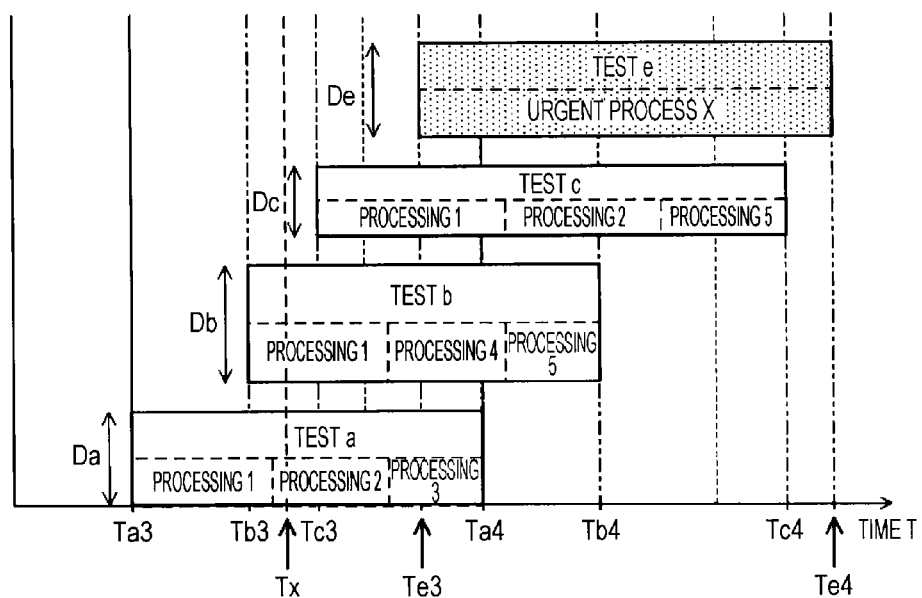
FIG. 15 is an example of the processing schedule of the image processing pertaining to Embodiment 2.

First, FIG. 15 is referred. FIG. 15 is an example of the image processing schedule pertaining to the present embodiment. FIG. 15 illustrates when reservation of "examination (test) e" is added as an urgent examination (test) in the time Tx while the image processing of examinations (studies) a, b, and c are reserved in server 2A. Furthermore, as illustrated in FIG. 15, the time Tx indicates the time when image processing of examination (test) a and b has already commenced, and before image processing of examination (test) c is carried out.

(Reservation Receiving Unit 111)

First, the reservation receiving unit 111 receives the reservation of examination (test) e. When the inspection items are determined as examination (test) e, the reservation receiving unit 111 accepts reservations in the same manner as Embodiment 1. However, in the case of urgent examinations (studies), there are cases when detailed inspection items are not decided. FIG. 16 is an example of a reservation management table comprising the reservation contents of an urgently added examination (test).

As illustrated in FIG. 16, in the case of urgent examinations, there are cases in which detailed conditions are not determined, as in the image processing classification C15, image size C16, and number of images C17. In such cases, the reservation receiving unit 111 accepts the imaging part identifier C12 of the modality 15 scheduled to photograph the image data, the test commencement time Te1, test termination time Te2, and return destination C18 as the test reservation. The reservation receiving unit 111 adds the information on examination e that accepted information for the reservation management table TBL10. Thereby, the reservation management table TBL10 is updated.

The reservation receiving unit 111 outputs the updated (with information on the examination e added) reservation management table TBL10 to the processing condition specifying part 112.

(Processing Condition Specifying Part 112)

When the processing condition specifying part 112 receives the reservation management table TBL10 from the reservation receiving unit 111, the process commencement time C41 and process termination time C42 of the imaging process are calculated regarding the newly added examination e. At this time, information on the image processing classification C15, image size C16, and number of images C17 are not input to the information on examination e. Accordingly, the condition for urgent processing is stored in advance in the processing condition specifying part 112 as the condition for, for example, "urgent processing x." The condition of urgent processing x comprises the time width Tx1 from commencement of the test to commencement of image processing and the processed data volume Dx. The time width Tx1 and data volume Dx are set by calculating the values estimated from statistics, etc. of urgent examinations carried out in the past, etc. The throughput calculator 12 is also referred to regarding the condition of urgent processing x. Accordingly, regarding the processing condition specifying part 112, the information is made available for reference to the throughput calculator 12. In addition, it is also possible to separately provide storage for storing conditions of the urgent processing x and have a configuration in which the processing condition specifying part 112 and throughput calculator 12 refers to the storage.

The processing condition specifying part 112 refers to the information on the image processing classification C15, image size C16, and the number of images C17 of the newly added examination e, and because this information is not input, it specifies the image processing of examination e as "urgent processing x." Furthermore, the identifier indicating the fact that it is "urgent" may be added as data, and whether or not the process is urgent may be determined from the identifier. Moreover, in this case, information on the image processing classification C15, image size C16, and number of images C17 may be input. The processing condition specifying part 112 calculates the time "Te3," which is the time following the "time width Tx1" set as the condition of "urgent processing x" from the "Te1" set as the test commencement time C13 of examination e, as the process commencement time C41. Moreover, the processing condition specifying part 112 specifies the time "Te4" as the process termination time C42 based on the time "Te2" set as the test termination time C14. The method for specifying the process termination time C42 is the same as Embodiment 1.

The processing condition specifying part 112 inputs the time "Te3" and time "Te4" specified as the process commencement time C41 and process termination time C42 as information on examination e to the process management table TBL40 that has already been generated during reservation of examinations a to c. That is, the process management table TBL40 is updated.

The processing condition specifying part 112 outputs the updated TBL40 to the throughput calculator 12 together with the reservation management table TBL10.

(Throughput Calculator 12)

The throughput calculator 12 calculates the throughput C43 regarding the newly added examination e when it receives the reservation management table TBL10 from the processing condition specifying part 112. The calculating method thereof is described in the following in detail.

First, the throughput calculator 12 refers to the image size C16 from the reservation management table TBL10 regarding the newly added examination e. At this time, the information on the image processing classification C15, image size C16, and number of images C17 is not input to the information on examination e. The throughput calculator 12 specifies the image processing of the examination as "urgent processing x" when information on the image size C16 cannot be read, and the total data volume for each test is specified as the data volume Dx set as the condition for "urgent processing x." Furthermore, when information on the image processing classification C15, image size C16, and number of images C17 are input, the total data volume of each test is calculated in the same manner as Embodiment 1.

Next, the throughput calculator 12 calculates the throughput C43 regarding examination e, based on the total data volume calculated as well as the process commencement time C41 and process termination time C42 stored in the process management table TBL40. The calculating method is the same as Embodiment 1. The calculated throughput C43 of examination e is "De." The throughput calculator 12 inputs the calculated throughput "De" of examination e to the "examination e" row in the process management table TBL40. Thereby, the process management table TBL40 is updated.

The throughput calculator 12 outputs the updated process management table TBL40 and reservation management table TBL10 to the analyzer 13.

(Analyzer 13)

The analyzer 13 receives the process management table TBL40 and reservation management table TBL10 from the throughput calculator 12, and outputs these to the request processing specifying part 131.

(Request Processing Specifying Part 131)

The request processing specifying part 131 receives the process management table TBL40 and updates the image processing schedule for each test carried out in server 2A based on the newly added information on the examination e. FIG. 15 shows the processing schedule with image processing information on examination e added.

Figure 18:
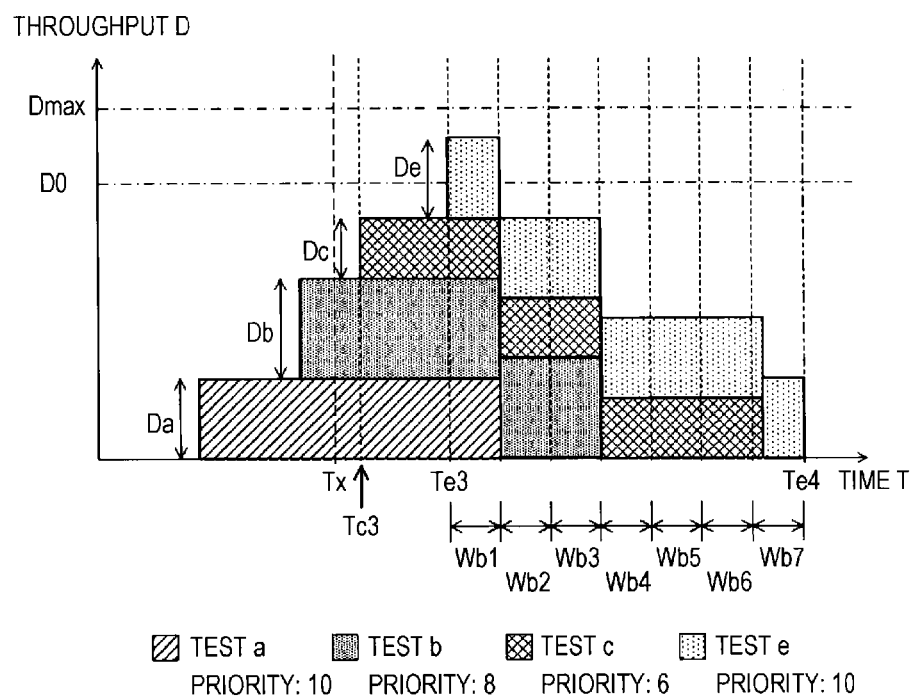
FIG. 18 is an example of the load predicting data pertaining to Embodiment 2.

The request processing specifying part 131 adds the image processing information on examination e to the load predicting data that has already been generated based on the image processing reservations of examinations a to c. The load predicting data is thereby updated. FIG. 18 is an example of the load predicting data updated along with the addition of image processing of examination e.

Next, the request processing specifying part 131 determines whether or not the total D of the throughput C43 of each image processing becomes the predicted throughput D0 or more between the process commencement times "Te3" to the process termination time "Te4" of the image processing of the added examination e. For example, in the example of FIG. 18, the time between the process commencement times "Te3" to the process termination time "Te4" is divided into time widths Wb1 to Wb7 with the unit time width determined in advance. In the example of FIG. 18, the total D becomes the predetermined throughput D0 or more at the time width Wb1.

The request processing specifying part 131 specifies the requested image processing to request substitution to the supporting server (that is, servers 2C or 2D) from among the image processing in which execution is scheduled at the specified time width Wb1. At this time, the request processing specifying part 131 preferentially specifies the image processing in which the process is not yet commenced as the requested image processing from among the image processing of examinations a to c reserved in advance. Specifically, the request processing specifying part 131 compares the time Tx with the process commencement time C41 of each test, and specifies the image processing commenced following the time Tx onwards. For example, in FIG. 18, image processing of examinations a and b is already commenced at time Tx. Accordingly, the request processing specifying part 131 specifies examination c. Next, the request processing specifying part 131 compares the priority of the specified examination c and the priority of the newly added examination e, and then specifies the image processing with low priority as the requested image processing. At this time, by means of setting high priority to the urgently added examination (for example, examination e), this examination is preferentially processed in the main server. In the example of FIG. 18, the request processing specifying part 131 specifies the image processing of examination c as the requested image processing.

Furthermore, when all image processing of examinations a to c have already commenced, the request processing specifying part 131 compares the priority of all image processing scheduled in the time width Wb1 (that is, examinations a to c and e), and specifies the image processing with the lowest priority as the requested image processing.

Once the image process to request substitution to the supporting server has been specified, the request processing specifying part 131 transmits the process management table TBL40 and reservation management table TBL10 to the request destination specifying part 132. At this time, the request processing specifying part 131 notifies the request destination specifying part 132 of the specified requested image process to request the supporting server (in the case of FIG. 18, the image processing of examination c) together.

(Request Destination Specifying Part 132)

The request destination specifying part 132 receives the process management table TBL40 and reservation management table TBL10 as well as the notification of the requested image process. The request destination specifying part 132 specifies any one from among servers 2C and 2D operating as the supporting server as the server to request the notified image processing. The process related to specifying the request destination is the same as Embodiment 1. Hereinafter, descriptions are provided assuming that "server 2C" has been specified as the new request destination.

The request destination specifying part 132 associates the specified request destination with the notified request image processing and the return destination C18 of the image data as one group. The request destination specifying part 132 outputs the generated group as well as the process management table TBL40 and reservation management table TBL10 to the request information manufacturer 133.

(Request Information Manufacturer 133)

The request information manufacturer 133 receives the request destination, request image processing, the group associated with the return destination C18, as well as the process management table TBL40 and reservation management table TBL10.

The request information manufacturer 133 generates the requested information E10 of the image processing of the newly added examination e, that is, the image process without the requested information E10. The method for generating the requested information E10 is the same as Embodiment 1.

Moreover, the request information manufacturer 133 specifies the image process with the altered request destination (that is, the image processing of examination c) based on the group of request destination, requested image processing, and return destination C18 received from the request destination specifying part 132. The request information manufacturer 133 updates the processing information E14 of the requested information E10 related to the image processing of the specified examination c. In the requested information E10 of examination c before update, "server 2A" is stored in the processing information E14 as the request destination E142. The request information manufacturer 133 updates the request destination E142 from "server 2A" to "server 2C", which is included in the newly received group as the request destination.

The request information manufacturer 133 outputs the generated and updated requested information as well as the process management table TBL40 and reservation management table TBL10 to the process controller 14.

(Process Controller 14)

The process controller 14 receives the generated and updated requested information as well as the process management table TBL40 and reservation management table TBL10 from the request information manufacturer 133.

The process controller 14 specifies the commencement time of the newly added examination e with reference to the reservation management table TBL10. The process controller 14 instructs the "modality 15A" indicated using the imaging part identifier C12 to commence photographing in correspondence with the specified test commencement time.

Moreover, the process controller 14 specifies the request unit 17 notifying of the generated and updated quested information E10 based on the reservation management table TBL10. For example, in the present embodiment, the process controller 14 receives the requested information E10 of examinations c and e. Accordingly, the process controller 14 specifies the "modality 15A" stored in the imaging part identifier C12 as the notification destination of the requested information E10 of examination e based on the reservation management table TBL10 illustrated in FIG. 16. Thereby, the process controller 14 specifies the request unit 17, which is associated to modality 15A and provided as the notification destination of the requested information E10 of examination e. Furthermore, examination c is the same as Embodiment 1, and the process controller 14 specifies the request unit 17 associated and stored in the image storage 16.

The process controller 14 refers to the process commencement time C41 of the process management table TBL40 and specifies the time at which the image processing of examinations c and e are commenced. The process controller 14 notifies the corresponding request unit 17 of the requested information on each of examinations c and e before the image processing of the test commences. Furthermore, the processes hereinafter are the same as in Embodiment 1.

Furthermore, the request destination specifying part 132 may specify the server 2 with a low processing load as the request destination based on the process load of servers 2A to 2D. In this case, a performance information notifying part 23, which notifies the processing load of the server as performance information, should be provided in servers 2A to 2D. Furthermore, the performance information may include information showing the transfer rate of the network. The information showing the transfer rate of the network may, for example, be specified based on the classification of the network, or the load of the network may be measured and calculated based on this.

The request destination specifying part 132 compares the performance information notified from the performance information notifying part 23 of servers 2A to 2D, thereby becoming capable of specifying the server 2 with a lower processing load as the request destination. By means of operating in this manner, those with lower processing load may be specified as the request destination when, for example, there are multiple request destination candidates.

Moreover, in the same manner as Modified Example 1, in the medical image processing system pertaining to the present embodiment as well, the request destination may be set to each process configuring the image processing.

In the abovementioned medical image processing system pertaining to the present embodiment, even when new reservations are added, the period of time during which the non-steady load increases including the added reservation as well as the image process carried out as the period of time may be specified, and some of the specified image processing may be requested to the supporting server.

As mentioned above, according to the medical image processing system pertaining to the present embodiment, the period of time during which the non-steady load increases and the image process carried out as the period of time may be specified, and some of the specified image processing may be requested to the supporting server. The supporting server is not required to constantly carry out image processing as the main server. Accordingly, it becomes possible to temporarily operate the server carrying out processes other than image processing as the supporting server and providing the supporting server provided on the external system. Thereby, correspondence to the load is achieved without having to install more main servers.

(Embodiment 3)

Next, as Embodiment 3, the charging process is described. Here, the load confirming part 140 is set inside the process controller 14. The load confirming part 140 obtains the charging rate of each server from the loading condition of servers 2C to 2F, selects the server with the lower charging rate, and returns this to the process controller 14. The process controller 14 requests processing to the server selected via the request destination specifying part 132. If processing is requested when the load of the request destination is low, it will be cheaply charged; therefore, it is a system to alternately request processes and alternately charge each other in, for example, institutes with a time lag with maximum loading such as overseas hospitals with a difference in time zone.

Figure 19:
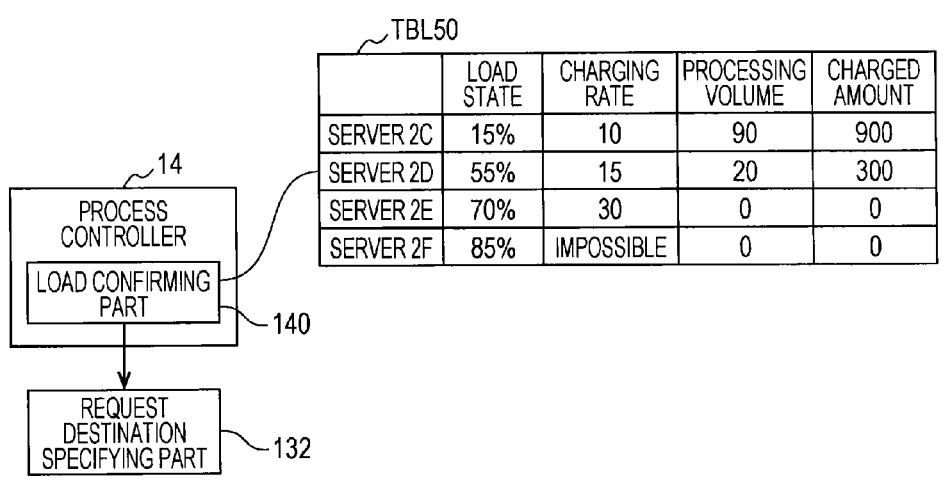
FIG. 19 is an example of the load confirmation unit pertaining to Embodiment 3.
Figure 20:
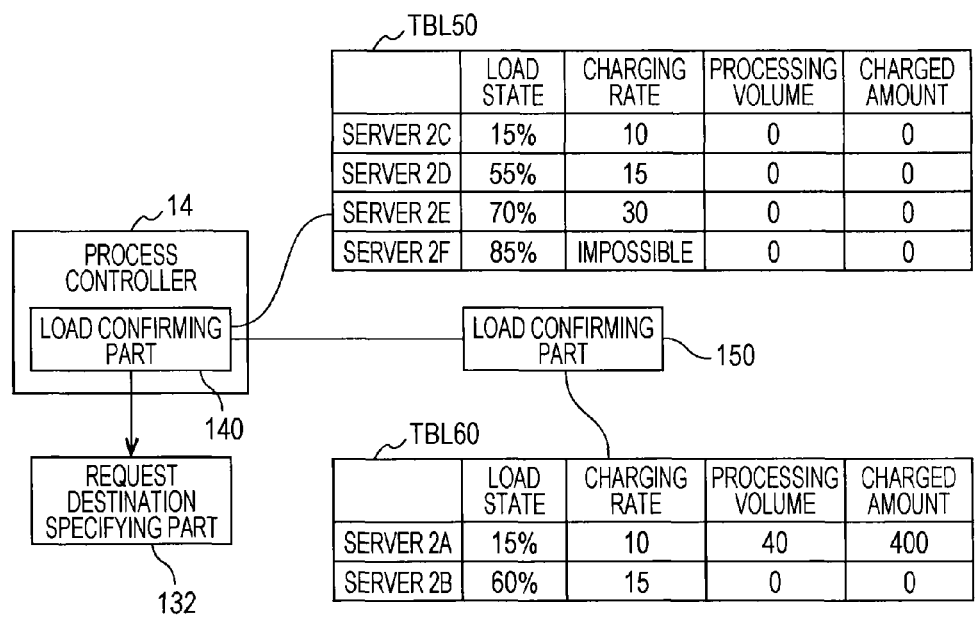
FIG. 20 is a modified example of the load confirmation unit pertaining to Embodiment 3.

The load confirming part 140 is illustrated in FIG. 19 and FIG. 20 as a processing function in the process controller 14 illustrated in FIG. 1; however, it may be provided as another processing part outside the process controller 14. The load confirming part 140 monitors respective servers 2C to 2F pertaining to the network outside the hospital in the same manner as the process controller 14 regardless of it being inside or outside the process controller 14, and transmits the monitored results to the process controller 14. While servers 2C and 2D are illustrated in FIG. 1, servers 2E and 2F are not illustrated; however, these servers are connected to the process controller 14 via the network in the same manner as servers 2C and 2D, becoming a partner for the processing request by the process controller 14.

First, the load confirming part 140 monitors respective servers 2C to 2F; thereby obtaining the loading condition of servers 2C to 2F. In the example illustrated in FIG. 19, the present loading condition of server 2C is 15%, the present loading condition of server 2D is 55%, the present loading condition of server 2E is 70%, and the present loading condition of server 2F is 85%.

The load confirming part 140 comprises the monitoring table TBL50 that monitors the present loading condition of the servers 2C to 2F. The monitoring table TBL50 further comprises a charging rate, throughput, and a charging amount. The load confirming part 140 confirms the charging rate of the servers 2C-2F. The charging rate is an example of the payment obtained by the load confirming part 140. The charging rate is, for example, in the case of the monitoring table TBL50, 10 if the loading condition is 20-50%, 15 if the loading condition is 50-65%, 30 if the loading condition is 65-80%, and the request is rejected when it exceeds 80%.

The value of the charging rate increases along with the increase in the loading condition. A particular charging rate may be set for each range of loading conditions as in the example mentioned above. A certain coefficient may be multiplied by the loading condition and this may be determined as the charging rate. The charging rate may be set from functions and graphs. The charging rate obtained in such a manner is transmitted to the process controller 14, and the process controller 14 specifies the request destination according to the charging rate.

In the example of the monitoring table TBL50, the charging rate of server 2C is the lowest; therefore, the process controller 14 may determine to transmit all processes to be transmitted to the external request destination to server 2C. Meanwhile, an upper limit may be set regarding the throughput to transmit to one server. For example, in the example of the monitoring table TBL50, the upper limit is set at 90. In this case, if the throughput to be requested is 110, the process controller 14 determines the throughput to be sent to server 2C with the lowest charging rate as 90, which is the upper limit, and sends the remaining 20 to server 2D with the second lowest charging rate. The evaluation result is sent to the request destination specifying part 132, and the request destination specifying part 132 carries out the requested process.

As a result, the load confirming part 140 obtains the charging amount by multiplying the throughput to the charging rate. The charging amount is an example of the payment obtained by the load confirming part 140. In the example of the monitoring table TBL50, the amount charged by server 2C becomes 900 and the amount charged by server 2D becomes 300. Servers 2E and 2F are not charged because they are not requested to carry out processing.

Moreover, by means of requesting processes, the loading condition of the server of the request destination increases, and may exceed the permissible amount at times. In this case, the loaded condition is monitored at a suitable time, and the process request is suspended when the loaded condition exceeds the permissible amount. Moreover, by means of requesting the process, the loading condition of the server of the request destination increases, and may exceed the permissible charging rate. For example, it may be possible that the loading condition, which was 48% before requesting, ultimately has a loading condition of 55% by means of requesting processes. In this case, separation is possible in which the throughput until the loading condition reaches 50% is multiplied by the amount when the loading condition is less than 50% (in this case, 10), and the throughput when the loading condition exceeds 50% is multiplied by the throughput when the loading condition is 50% or more (in this case, 15).

Meanwhile, the load confirming part 140 may determine the charging amount based on the maximum load for each requested process. For example, it is supposed that the maximum value of the load state of the server 2C is 52% if all amounts of process 110 are requested to the server 2C with the lowest charging rate. In this case, the processed amount 110 is multiplied by 15 to 1650 as a total. Meanwhile, the load confirming part 140 may determine the processed amount 90 to be sent to the server 2C with the lowest charging rate, resulting in multiplying 90 by 10 to 100 in the server 2C and multiplying 20 by 15 to 300 in the server 2D, so as to be totally 1200, which is cheaper than requesting all the processed amount 110 to the server 2C.

By means of configuring in this manner, appropriate processing load distribution becomes possible upon appropriate charging according to the amount of requesting processing and the condition of the requested destination.

Next, an example of the servers alternately charging each other by means of alternately carrying out the requested processing is described with reference to FIG. 20. In the case of the example using FIG. 19, a case was described when being one-sidedly charged from requesting to an external server. Conversely, when the processing load of servers 2A and 2B is small and the processing load of external servers 2C to 2F is large, charging is possible in contrast by means of accepting processing request from the outside. In this manner, the processing allotment may be alternated, such as the requesting process and being charged in certain cases and receiving the request for processing and charging in other cases.

The load confirming part 140 of the in-hospital network is monitoring servers 2C to 2F, as described using FIG. 19, and is managed by the monitoring table TBL50. Meanwhile, the system of servers 2C and 2D as well as the system of servers 2E and 2F connected to the network outside the hospital are also each provided with the load confirming part 150, and comprises the monitoring table TBL60. The load confirming part 150 of each system is monitoring the loading condition of servers 2A and 2B.

In the example of FIG. 20, a processing request is not sent to the in-hospital network system; therefore, the throughput and charging amount shown in the monitoring table TBL50 are both 0. In this state, the load confirming part 150 of the network outside the hospital confirms the 15% loading condition of server 2A and the 60% loading condition of server 2B. The load confirming part 150 obtains the charging rates 10% and 15% from each obtained loading condition value. Then, the process controller (not illustrated, corresponds to the process controller 14 in the in-hospital network) selects server 2A with the low charging rate. Then, the throughput 40 is carried out by server 2A, making the charging amount 400. These are monitored by the monitoring table TBL60.

By means of configuring in this manner, the servers are capable of alternately requesting processes and alternately charging each other; therefore, the processing load may be dispersed in addition to appropriately charging when there is a deviation in the amount of load upon the total amount of processes.

While certain embodiments have been described, these embodiments have been presented by way of example only, and are not intended to limit the scope of the inventions. Indeed, the novel systems described herein may be embodied in a variety of their forms; furthermore, various omissions, substitutions and changes in the form of the systems described herein may be made without departing from the spirit of the inventions. The accompanying claims and their equivalents are intended to cover such forms or modifications as would fall within the scope and spirit of the inventions.

What is claimed is:

1. A medical image processing system comprising a plurality of servers each having an image processing circuit, wherein the servers execute in parallel a plurality of image processes on image data, the medical image processing system comprising:
   a reservation manager circuit configured to receive information of a reservation for image processing, and to manage a process commencement time and a process termination time of the image processing and a volume of the image data to be processed by the image processing, based on the information of the reservation,
   a throughput calculating circuit configured to calculate a throughput to be processed per predetermined time period for the image processing based on the volume of the image data, the process commencement time, and the process termination time, for a first server from among the plurality of servers,
   an analyzing circuit configured to calculate, prior to obtaining the image data, a throughput total of image processing to be carried out in parallel on the first server for respective time periods, based on the volume of the image data, the process commencement time, and the process termination time of the image processing, and to specify, from among all image processes to be carried out by the first server, a first image process to not be performed by the first server so that the throughput total of the first server during each of the respective time periods becomes less than a predetermined throughput, when the calculated throughput total exceeds the predetermined throughput, and
   a request circuit configured to assign the first image process to a second server different from the first server.

2. The medical image processing system according to claim 1, wherein
   the reservation manager circuit is further configured to weigh the image processing carried out on the first server based on instructions from an operator, after receiving the reservation, and
   the analyzing circuit is configured to specify the first image process based on the weighing.

3. The medical image processing system according to claim 1, further comprising a photographing apparatus configured to photograph a subject to generate the image data, wherein
   the reservation manager circuit is further configured to calculate an exposure time required to photograph the subject based on the volume included in the reservation, in response to the reservation comprising a commencement time and a termination time of photographing in the photographing apparatus and an amount of the image data to be photographed, and to specify the process commencement time and the process termination time based on the exposure time, the commencement time, and the termination time of the photographing.

4. The medical image processing system according to claim 1, further comprising a memory that stores the image data, wherein
   the reservation manager circuit receives the reservation comprising the process commencement time and the process termination time with respect to the image data stored in the memory.

5. The medical image processing system according to claim 1, wherein, when the reservation manager circuit newly receives a new reservation of the image processing after the first image process is assigned to the second server,
   the analyzing circuit calculates the throughput total of the image processing carried out in the first server between the process commencement time and the process termination time of the newly received reservation, and
   when the throughput total is more than the predetermined throughput, the analyzing circuit specifies a second image process to be assigned to the second server, from among all the image processes carried out by the first server.

6. The medical image processing system according to claim 1, wherein
   the plurality of servers are included in a server group configured to carry out image processing of different categories, and
   the analyzing circuit is further configured to store in advance the different categories of the image processing executable by all servers included in the server group, and to specify, as the second server, a server in which the first image process is executable from among the servers in the server group, based on the different categories of the first image process.

7. The medical image processing system according to claim 5, wherein
   the plurality of servers comprise a server group, each comprising a notifying unit that notifies a processing load of the servers to the analyzing circuit, and
   the analyzing circuit specifies the second server from among the servers in the server group, based on the processing load.

8. The medical image processing system according to claim 1, further comprising:
   a load confirmation circuit configured to monitor a load condition of the other servers to determine a payment for executing the first image process based on a throughput of the first image process.

9. The medical image processing system according to claim 6, wherein
   the plurality of servers each comprise a load confirmation circuit configured to monitor the load condition of the other servers connected to the network to determine a payment for executing the first image process based on a throughput of the first image process.

* * * * *